(12) United States Patent
Cervin et al.

(10) Patent No.: US 8,852,890 B2
(45) Date of Patent: Oct. 7, 2014

(54) PRODUCTION OF BACTERIAL STRAINS

(75) Inventors: Marguerite A. Cervin, Palo Alto, CA (US); Philippe Soucaille, Deyme (FR); Donald E. Trimbur, Palo Alto, CA (US); Fernando Valle, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 1132 days.

(21) Appl. No.: 12/171,762

(22) Filed: Jul. 11, 2008

(65) Prior Publication Data
US 2009/0075347 A1   Mar. 19, 2009

Related U.S. Application Data

(63) Continuation of application No. 10/527,827, filed as application No. PCT/US03/31445 on Oct. 3, 2003, now abandoned.

(60) Provisional application No. 60/416,167, filed on Oct. 4, 2002, provisional application No. 60/416,192, filed on Oct. 4, 2002.

(51) Int. Cl.
| | |
|---|---|
| C12P 21/00 | (2006.01) |
| C12P 7/06 | (2006.01) |
| C12P 7/28 | (2006.01) |
| C12P 7/40 | (2006.01) |
| C12P 7/46 | (2006.01) |
| C12N 15/70 | (2006.01) |
| C12P 7/44 | (2006.01) |
| C12P 7/20 | (2006.01) |
| C07K 14/24 | (2006.01) |
| C12P 13/04 | (2006.01) |
| C12P 7/18 | (2006.01) |
| C12P 13/22 | (2006.01) |

(52) U.S. Cl.
CPC ............... *C07K 14/24* (2013.01); *C12P 7/065* (2013.01); *C12P 7/28* (2013.01); *C12P 7/40* (2013.01); *C12P 7/46* (2013.01); *C12N 15/70* (2013.01); *Y02E 50/17* (2013.01); *C12P 7/44* (2013.01); *C12P 7/20* (2013.01); *C12P 7/06* (2013.01); *C12P 13/04* (2013.01); *C12P 7/18* (2013.01); *C12P 13/22* (2013.01)
USPC ........................................................ 435/70.1

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,760,025 A | 7/1988 | Estell et al. | |
| 5,032,514 A | 7/1991 | Anderson et al. | |
| 5,168,056 A | 12/1992 | Frost et al. | |
| 5,272,073 A | 12/1993 | Frost et al. | |
| 5,374,543 A | 12/1994 | Murdock | |
| 5,487,987 A | 1/1996 | Frost et al. | |
| 5,494,816 A | 2/1996 | Murdock | |
| 5,602,030 A | 2/1997 | Ingrahm et al. | |
| 5,629,181 A | 5/1997 | Frost et al. | |
| 5,686,276 A | 11/1997 | Laffend et al. | |
| 5,776,736 A | 7/1998 | Frost et al. | |
| 5,985,617 A | 11/1999 | Liao | |
| 6,013,494 A | 1/2000 | Nakamura et al. | |
| 6,136,576 A | 10/2000 | Diaz-Torres et al. | |
| 6,432,686 B1 | 8/2002 | Bulthuis et al. | |
| 6,472,169 B1 | 10/2002 | Frost et al. | |
| 6,962,794 B2 | 11/2005 | Valle et al. | |
| 7,132,527 B2 | 11/2006 | Payne et al. | |
| 7,371,558 B2 * | 5/2008 | Cervin et al. ............ | 435/252.33 |
| 2002/0168654 A1 | 11/2002 | Maranas et al. | |
| 2005/0147968 A1 | 7/2005 | Payne et al. | |
| 2005/0208615 A1 | 9/2005 | Wilkins et al. | |

FOREIGN PATENT DOCUMENTS

| | | |
|---|---|---|
| EP | 1170376 | 1/2002 |
| WO | WO 87/01130 | 2/1987 |
| WO | WO 96/34961 | 11/1996 |
| WO | WO 96/35796 | 11/1996 |
| WO | WO 98/07846 | 2/1998 |
| WO | WO 98/21339 | 5/1998 |
| WO | WO 98/21347 | 5/1998 |
| WO | WO 99/28480 | 6/1999 |
| WO | WO 01/12833 | 2/2001 |
| WO | WO 03/089604 | 10/2003 |

OTHER PUBLICATIONS

Overkamp et al ("Metabolic Engineering of Glycerol Production in *Saccharomyces cerevisiae*"; Applied and Environmental Microbiology, Jun. 2002, pp. 2814-2821).*

Canonaco et al ("Metabolic flux response to phosphoglucose isomerase knock-out in *Escherichia coli* and impact of overexpression of the soluble transhydrogenase UdhA"; FEMS Microbiology Letters, 2001, pp. 247-252).*

Hernandez-Montalvo et al in "Characterization of sugar mixtures utilization by an *Escherichia coli* mutant devoid of the phosphotransferase system" (Appl Microbiol Biotechnol: vol. 57, pp. 186-191; Published online: Jul. 24, 2001).*

Nystrom et al in "Bacterial defense against aging: role of the *Escherichia coil* ArcA regulator in gene expression, readjusted energy flux and survival during stasis" (in EMBO, vol. 15, No. 13, pp. 3219-3228, 1996).*

Iuchi (1988).*

Iuchi (1996.*

Culham et al in "The osmotic stress response and virulence in pyelonephritis isolates of *Escherichia coli*: contributions of RpoS, ProP, ProU and other systems" (Microbiology, Jun. 2001, vol. 147, 1657-1670, whole article).*

(Continued)

*Primary Examiner* — Michele K Joike
*Assistant Examiner* — Mindy G Brown
(74) *Attorney, Agent, or Firm* — Danisco US Inc.

(57) ABSTRACT

The present invention provides methods to enhance production of desired products and increase the growth rate of a bacterial strain by inactivating an endogenous arcA and optionally overexpressing a ppc gene.

8 Claims, 16 Drawing Sheets

(56) References Cited

OTHER PUBLICATIONS

Golovlev and Golovleva in "Physiology of Microbial Cells and Metabolic Engineering" (Microbiology, 2000, vol. 69, pp. 119-128, whole article).*

Chou et al (1996) in "Genetic Manipulation of Stationary-Phase Genes to Enhance Recombinant Protein Production in *Escherichia coli*" (Biotechnology and Bioengineering, vol. 50, pp. 636-642, whole article).*

Hernandez-Montavalo et al., Appl Microbiol Biotechnol, 2001, vol. 57, pp. 186-191.*

Miroux et al., J. Mol. Biol., 1996, vol. 260, pp. 289-298.*

Johansson et al., Applied Microbiology and Biotechnology, 1984, vol. 20, pp. 105-110.*

Iuchi et al., PNAS, 1988, vol. 85, pp. 1888-1892.*

Kato, Journal of Molecular Catalysis, 1999, vol. 6, p. 223-233.*

Yang, Yea-Tyng et al., Biotechnology and Bioengineering, 1999, vol. 65, pp. 291-297.*

Altschul, S.F. et al. "Gapped BLAST and PSI—BLAST: a new generation of protein database search programs." *Nucleic Acids Res.* 25: 3389-3402, 1997.

Amann, E. et al. "Vectors bearing a hybrid trp-lac promoter useful for regulated expression of cloned genes in *Escherichia coli*." *Gene* 25(2-3): 167-78, Nov. 1983.

Amore, R. et al. "The fermentation of xylose—an analysis of the expression of *Bacillus* and *Actinoplanes xylose* isomerase genes in yeast." *Appl. Microbiol. Biotechnol.* 30(4): 351-357, Apr. 1, 1989.

Báez, J.L. et al. "Determination of 3-deoxy-D-arabino-heptulosonate 7-phosphate productivity and yield from glucose in *Escherichia coli* devoid of the glucose phosphotransferase transport system." *Biotechnol. Bioeng* 73(6): 530-535, 2001.

Báez-Viveros, J.L. et al. "Metabolic engineering and protein directed evolution increase the yield of L-phenylalanine synthesized from glucose in *Escherichia coli*." *Biotechnol. Bioeng* 87(4): 516-24, Aug. 20, 2004.

Bouvet, O.M. et al. "Diversity of the phosphoenolpyruvate/glucose phosphotransferase system in the Enterobacteriaceae." *Ann. Inst. Pasteur Microbiol* 138(1): 3-13, 1987.

Burr, T. et al. "DNA sequence elements located immediately upstream of the 210 hexamer in *Escherichia coli* promoters: a systematic study." *Nucleic Acids Res* 28: 1864-1870, 2000.

Carrier, T.A. et al. "Controlling Messenger RNA Stability in Bacteria: Strategies for Engineering Gene Expression." *Biotechnol. Prog.* 13(6): 699-708, Dec. 2, 1997.

Chao, Y.P. et al. "Alteration of growth yield by overexpression of ppc and pck in *Escherichia coli*." *Appl. Environ. Microbiol* 59: 4261-4265, 1993.

Chou, C.-H. et al. "Genetic manipulation of stationary-phase genes to enhance recombinant protein production in *Escherichia coli*." *Biotechnol. Bioeng.* 50(6): 636-642, 1996.

Conway, T. et al. "Locations of the zwf, edd, and eda genes on the *Escherichia coli* physical map." *J Bacteriol.* 173(17): 5247-5248, Sep. 1991.

Cooper, R.A. "Metabolism of methylglyoxal in microorganisms." *Annu. Rev. Microbiol* 38: 49-68, 1984.

Cordaro, J.C. et al. Fosfomycin resistance: selection method for internal and extended deletions of the phosphoenolpyruvate:sugar phosphotransferase genes of *Salmonella typhimurium* . . . *Journal of Bacteriology* 128(3): 785-793, Dec. 1976.

Cunningham, L. et al. "Transcription and transcript processing in the sdhCDAB-sucABCD operon of *Escherichia coli*." *Microbiology* 144(8): 2113-2123, Aug. 1, 1998.

Datsenko, K.A. et al. "One-step inactivation of chromosomal genes in *Escherichia coli* using PCR products." *Proc Natl Aced Sci USA* 97: 6640-6645, 2000.

De Reuse, H. et al. "The ptsH, ptsI, and crr genes of the *Escherichia coli* phosphoenolpyruvate-dependent phosphotransferase system: a complex operon with several modes of transcription." *J Bacteriol.* 170(9): 3827-3837, Sep. 1988.

De Spiegeleer, B. et al. "Direct assay for phosphotransacetylase and acetyl-coenzyme a carboxylase by high-performance performance liquid chromatography." *Analytical Biochemistry* 158(1): 195-200, Oct. 1986.

Diaz-Ricci, J.C. et al. "Effect of alteration of the acetic acid synthesis pathway on the fermentation pattern of *Escherichia coli*." *Biotechnol. Bioeng* 38(11): 1318-1324, 1991.

Egan, S.E. et al. "Molecular characterization of the Entner-Doudoroff pathway in *Escherichia coli*: sequence analysis and localization of promoters for the edd-eda operon." *J. Bacteriol.* 174(14): 4638-4646, Jul. 1, 1992.

Ferguson, G.P. "Protective mechanisms against toxic electrophiles in *Escherichia coli*." *Trends in Microbiology* 7(6): 242-247, Jun. 1, 1999.

Ferguson, G.P. et al. "Methylglyoxal production in bacteria: suicide or survival?." *Archives of Microbiology* 170(4): 209-218, 1998.

Flores, C.-L. et al. "Expression of PEP carboxylase from *Escherichia coli* complements the phenotypic effects of pyruvate carboxylase mutations in *Saccharomyces cerevisiae*." *FEBS Letters* 412(3): 531-534, Aug. 4, 1997.

Flores, N. et al. "Adaptation for fast growth on glucose by differential expression of central carbon metabolism and gal regulon genes in an *Escherichia coli* strain lacking the phosphoenolpyruvate:carbohydrate phosphotransferase system." *Metab. Eng* 7(2): 70-87, Mar. 2005.

Fox, D. et al. "Regulation of sugar transport by the bacterial phosphoenolpyruvate: glucose phosphotransferase system." *Biochem. Soc. Trans* 12(2): 155-7, Apr. 1984.

Gachelin, G. "A new assay of the phosphotransferase system in *Escherichia coli*." *Biochem. Biophys. Res. Commun* 34(4): 382-7, Feb. 21, 1969.

Gosset, G. et al. "A direct comparison of approaches for increasing carbon flow to aromatic biosynthesis in *Escherichia coli*." *J. Ind. Microbiol* 17(1): 47-52, Jul. 1996.

Hanahan, D. "Studies on transformation of *Escherichia coli* with plasmids." *J. Mol. Biol* 166(4): 557-80, Jun. 5, 1983.

Hengge-Aronis, R. "Regulation of Gene Expression during Entry into Sationary Phase." In *Escherichia coli and Salmonella: Cellular and Molecular Biology*, edited by F.C. Neidhardt et al., pp. 1497-1512. Washington, D.C.: ASM Press, 1996.

Hengge-Aronis, R. "Signal Transduction and Regulatory Mechanisms Involved in Control of the σS (RpoS) Subunit of RNA Polymerase." *Microbiol. Mol. Biol. Rev.* 66(3): 373-395, Sep. 1, 2002.

Hernández-Montalvo, V. et al. "Characterization of sugar mixtures utilization by an *Escherichia coli* mutant devoid of the phosphotransferase system." *Appl. Microbiol. Biotechnol.* 57(1): 186-191, Oct. 1, 2001.

Hernández-Montalvo, V. et al. "Expression of galP and glk in a *Escherichia coli* PTS mutant restores glucose transport and increases glycolytic flux to fermentation products." *Biotechnol. Bioeng* 83(6): 687-94, Sep. 20, 2003.

Hoess, R.H. et al. "The role of the loxP spacer region in PI site-specific recombination." *Nucl. Acids Res.* 14(5): 2287-2300, Mar. 11, 1986.

Huang, L.C. et al. A bacterial model system for chromosomal targeting . . . *Nucleic Acids Res.* 19(3): 443-448, Feb. 11, 1991.

Huffman, K.E. et al. "DNA-sequence asymmetry directs the alignment of recombination sites in the FLP synaptic complex." *J. Mol. Biol* 286(1): 1-13, Feb. 12, 1999.

Iuchi, S. et al. "Adaptation of *Escherichia coli* to redox environments by gene expression." *Mol. Microbiol* 9(1): 9-15, Jul. 1993.

Iuchi, S. et al. "arcA (dye), a global regulatory gene in *Escherichia coli* mediating repression of enzymes in aerobic pathways." *Proc. Natl. Acad. Sci. USA* 85(6): 1888-92, Mar. 1988.

Jeon, Y. et al. "Multimerization of Phosphorylated and Non-phosphorylated ArcA Is Necessary for the Response Regulator Function of the Arc Two-component Signal Transduction System." *J. Biol. Chem.* 276(44): 40873-40879, Oct. 26, 2001.

Kageyama, B. et al. "*Pantoea punctata* sp. nov., *Pantoea citrea* sp. nov., and *Pantoea terrea* sp. nov. isolated from fruit and soil samples." *Int. J. Syst. Bacteriol* 42(2): 203-10, Apr. 1992.

(56) References Cited

OTHER PUBLICATIONS

Kilby, N.J. et al. "Site-specific recombinases: tools for genome engineering." *Trends Genet* 9(12): 413-21, Dec. 1993.
Kramer, W. et al. "The gapped duplex DNA approach to oligonucleotide-directed mutation construction." *Nucl. Acids Res.* 12(24): 9441-9456, Dec. 21, 1984.
Lévy, S. et al. "Cyclic AMP synthesis in *Escherichia coli* strains bearing known deletions in the pts phosphotransferase operon." *Gene* 86(1): 27-33, Jan. 31, 1990.
Lynch, A.S. et al. "Regulation of aerobic and anaerobic metabolism by the Arc system." In *Regulation of Gene Expression in Escherichia coli*, edited by E.C.C. Lin et al., pp. 361-381. New York: Chapman and Hall, 1996.
McCann, M.P. et al. "The putative sigma factor KatF has a central role in development of starvation-mediated general resistance in *Escherichia coli*." *J Bacteriol.* 173(13): 4188-4194, Jul. 1991.
Meadow, N.D. et al. "The bacterial PEP glycose phosphotransferase system." *Annu. Rev. Biochem* 59: 497-542, 1990.
Mermod, N. et al. Vector for regulated expression of cloned genes in a wide range of gram-negative bacteria . . . *J Bacteriol.* 167(2): 447-454, Aug. 1986.
Miller, J.E. et al. "Production of phenylalanine and organic acids by PEP carboxylase deficient mutants of *Escherichia coli*." *J. Ind. Microbiol* 2: 143-149, 1987.
Morinaga, Y. et al. "Improvement of Oligonucleotide-Directed Site-Specific Mutagenesis Using Double-Stranded Plasmid DNA." *Bio/Technology* 2(7): 636-639, Jul. 1984.
Müller, J. et al. "Repression of lacPromoter as a Function of Distance, Phase and Quality of an Auxiliary lac Operator." *J. Mol. Biol* 257(1): 21-29, Mar. 22, 1996.
Nunes-Duby, S.E. et al. "Similarities and differences among 105 members of the Int family of site-specific recombinases." *Nucl. Acids Res.* 26(2): 391-406, Jan. 15, 1998.
Nyström, T. et al. Bacterial defense against aging: role of the *Escherichia coli* ArcA regulator in gene expression, readjusted energy flux and survival during stasis . . . *EMBO J.* 15(13): 3219-3228, Jul. 1, 1996.
Palmeros, B. et al. "A family of removable cassettes designed to obtain antibiotic-resistance-free genomic modifications of *Escherichia coli* and other bacteria." *Gene* 247(1-2): 255-264, Apr. 18, 2000.
Pearson, W.R. et al. "Improved Tools for Biological Sequence Comparison." *Proc. Natl. Acad. Sci. USA* 85(8): 2444-2448, Apr. 15, 1988.
Peekhaus, N. et al. "What's for Dinner?: Entner-Doudoroff Metabolism in *Escherichia coli*." *J Bacterial.* 180(14): 3495-3502, Jul. 1998.
Perrenoud, A. et al. "Impact of Global Transcriptional Regulation by ArcA, ArcB, Cra, Crp, Cya, Fnr, and Mlc on Glucose Catabolism in *Escherichia coli*." *J. Bacterial.* 187(9): 3171-3179, May 1, 2005.
Porath, J. "Immobilized metal ion affinity chromatography." *Protein Expr Purif* 3(4): 263-81, 1992.
Postma, P.W. et al. "Phosphoenolpyruvate:carbohydrate phosphotransferase systems of bacteria." *Microbiol. Mol. Biol. Rev.* 57(3): 543-594, Sep. 1, 1993.
Potter, H. "Electroporation in biology: Methods, applications, and instrumentation." *Anal. Chem.* 174(2): 361-373, Nov. 1, 1988.
Prohl, C. et al. "Functional citric acid cycle in an arcA mutant of *Escherichia coli* during growth with nitrate under anoxic conditions." *Arch. Microbial.* 170(1): 1-7, Jun. 18, 1998.
Romano, A.H. et al. "Distribution of the phosphoenolpyruvate:glucose phosphotransferase system in fermentative bacteria." *J Bacterial.* 139(1): 93-97, Jul. 1979.
Russell, D.R. et al. "Construction and analysis of in vivo activity of *E. coli* promoter hybrids and promoter mutants that alter the -35 to -10 spacing." *Gene* 20(2): 231-43, Dec. 1982.
Saffen, D.W. et al. "Sugar transport by the bacterial phosphotransferase system. Molecular cloning and structural analysis of the *Escherichia coli* ptsH, ptsI, and crr genes." *J. Biol. Chem.* 262(33): 16241-16253, Nov. 25, 1987.

Saier, M.H. et al. "Energetics of the bacterial phosphotransferase system in sugar transport and regulation of carbon metabolism." In *Bacterial Energetics*, edited by T.A. Krulwich, pp. 279-299. San Diego, CA: Academic Press, 1990.
Sauer, B. "Site-specific recombination: developments and applications." *Current Opinion in Biotechnology* 5(5): 521-527, Oct. 1994.
Silhavy, T.J. et al. *Experiments with Gene Fusions*. pp. 111-112. New York: Cold Spring Harbor Press, 1984.
Sommer, N. et al. "T4 early promoter strength probed in vivo with unribosylated and ADP-ribosylated *Escherichia coli* RNA polymerase: a mutation analysis." *Microbiology* 146(10): 2643-2653, Oct. 1, 2000.
Sternberg, N. et al. "Bacteriophage P1 site-specific recombination: I. Recombination between IoxP sites." *J. Mol. Biol* 150(4): 467-486, Aug. 25, 1981.
Sweeney, N.J. et al. "The *Escherichia coli* K-12 gntP gene allows *E. coli* F-18 to occupy a distinct niche in the streptomycin-treated mouse large intestine." *Infect. Immun* 64: 3497-3503, 1996.
Taha, T.S.M. et al. "Detection of Metabolites of the Entner-Doudoroff Pathway by HPLC with Pulsed Amperometry: Application to Assays for Pathway Enzymes." *Analytical Biochemistry* 219(1): 115-120, May 15, 1994.
Valle, F. et al. "Overexpression of Chromosomal Genes in *Escherichia coli*." In *Recombinant Gene Expression: Reviews and Protocols*, edited by P. Balbas et al., pp. 113-122. Methods in Molecular Biology 267. New York: Humana Press, 2004.
Weigel, N. et al. "Sugar transport by the bacterial phosphotransferase system. Isolation and characterization of enzyme I from *Salmonella typhimurium*." *J. Biol. Chem.* 257(23): 14461-14469, 1982.
Wyborn, N.R. et al. "Expression of the *Escherichia coli* yfiD gene responds to intracellular pH and reduces the accumulation of acidic metabolic end products." *Microbiology* 148(4): 1015-1026, Apr. 1, 2002.
Yanisch-Perron, C. et al. "Improved M13 phage cloning vectors and host strains: nucleotide sequences of the M13mp18 and pUC19 vectors." *Gene* 33(1): 103-19, 1985.
Zhu, X.D. et al. "Homology requirements for ligation and strand exchange by the FLP recombinase." *J. Biol. Chem.* 270(19): 11646-11653, May 12, 1995.
Iuchi et al., "The arcB gene of *Escherichia coli* encodes a sensor-regulator protein for anaerobic repression of the arc modulo", Mol. Microbiol, (1990), 4:715-727.
U.S. Appl. No. 08/307,371, Sep. 16, 1994, Liao.
Allenza et al: "Psuedomonas cepacia mutants blocked in the Enter-Doudoroff pathway.", Journal of Bacteriology, vol. 150, No. 3, Jun. 1, 1982, pp. 1340-1347, XP55016299, ISSN: 0021-9193.
Arora et al. "Glucokinase of *Escherichia coli*: Induction in Response to the Stress of Overexpressing Foreign Proteins," Archives of Biochemistry Biophysics 319(2):574-578, 1995.
Deuschle et al., "Promoters of *Escherichia coli*: a hierarchy of in vivo strength indicates alternate structures", (1986) EMBO J. 5:2987-2994.
Flores et al. "Analysis of Carbon Metabolism in *Eschericia coli* Strains with an Inactive Phosphotransferase System by 13C Labeling and NMR Spectroscopy," Metabolic Eng. 4:124-137, 2002.
Flores et al. "Pathway Engineering for the production of aromatic compounds in *Eschericia coli*," *Nature Biotechnology* 14:620-623, 1996.
Garcia-Aller et al. "The glucose-specific carrier of the *Eschericia coli* phosphtransferase system," *Eur. J. Biochem.* 269:4969-4980, 2002.
Jahreis et al. "Adaptation of Sucrose Metabolism in the *Eschericia coli* Wild-type Strain EC3132," *J Bacteriology* 184:5307-5316, 2002.
Kim et al "A 20 nucleotide upstream clement is essential for the nopaline synthase (nos) promoter activity," *Plant Molecular Biology* 24:105-117, 1994.
Seta et al. "Characterization of *Echerichia coli* strains with gapA and gapB genes detected," J. Bacteriol. 173:5218-5221, 1997.
Van Der Rest et al., "Functions of the Membrane-Associated and Cytoplasmic Malate Dehydrogenases in the Citric Acid Cylce of *E. Coli*", Dec. 2000, vol. 182, No. 24, pp. 6892-6899.

* cited by examiner

Reaction 1:

Glucose $\xrightarrow{\text{Glycolysis}}$ 2 Pyruvate + 0 ATP + 2 NADH

Reaction 2:

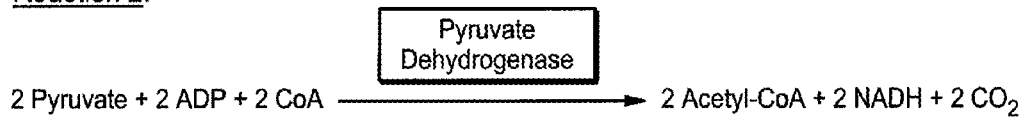

2 Pyruvate + 2 ADP + 2 CoA $\xrightarrow{\text{Pyruvate Dehydrogenase}}$ 2 Acetyl-CoA + 2 NADH + 2 $CO_2$ Reaction 3:

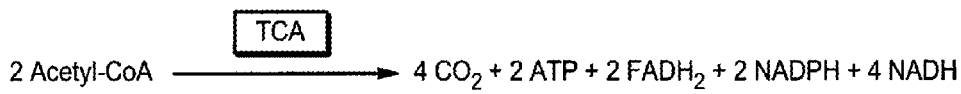

2 Acetyl-CoA $\xrightarrow{\text{TCA}}$ 4 $CO_2$ + 2 ATP + 2 $FADH_2$ + 2 NADPH + 4 NADH Reaction 4:

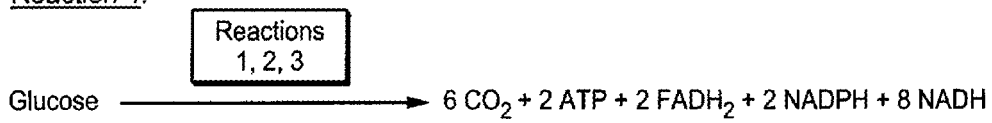

Glucose $\xrightarrow{\text{Reactions 1, 2, 3}}$ 6 $CO_2$ + 2 ATP + 2 $FADH_2$ + 2 NADPH + 8 NADH Reaction 5:

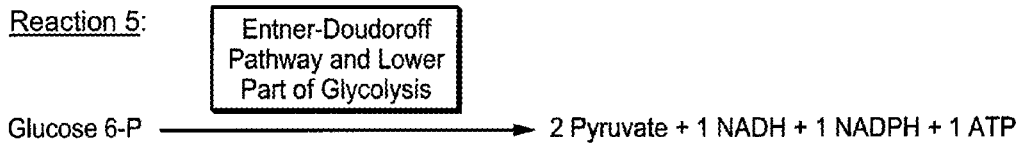

Glucose 6-P $\xrightarrow{\text{Entner-Doudoroff Pathway and Lower Part of Glycolysis}}$ 2 Pyruvate + 1 NADH + 1 NADPH + 1 ATP

*FIG. 1B*

(a) SEQ ID NO. 1
ArcA1
CACATTCTTATCGTTGAAGACGAGTTGGTAACACGCAACACGTGTAGGCTGGAGCTGCTTC (b) SEQ ID NO. 2
ArcA2
TTCCAGATCACCGCAGAAGCGATAACCTTCACCGTGAATGGTCATATGAATATCCTCCTTAG (c) SEQ ID NO. 3
ArcA3
AGTTGGTAACACGCAACACGCAAC (d) SEQ ID NO. 4
ArcA4
CGCAGAAGCGATAACCTTCACCG (e) SEQ ID NO. 5
Edd1
ATGAATCCACAATTGTTACGCGTAACAAATCGAATCATTGAACGTTCGCGCGAGACTCGCTCTG
CTTATCTCGCCCGGATTTATCGATAAGCTGGATCC (f) SEQ ID NO. 6
Edd2
TTAAAAAGTGATACAGGTTGCGCCCTGTTCGGCACCGGACAGTTTTTCACGCAAGGCGCTGAAT
AATTCACGTCCTGTCGGATGCATATGGCGGCCGC (g) SEQ ID NO. 7
Edd3
TAACATGATCTTGCGCAGATTG (h) SEQ ID NO. 8
Edd4
ACTGCACACTCGGTACGCAGA (i) SEQ ID NO. 9
DackA-F
ATGTCGAGTAAGTTAGTACTGGTTCTGAACTGCGGTAGTTCTTCACTGAAATTTGCCATCATCG
ATGCAGTAAATGGTGATGTGTAGGCTGGAGCTGCTT

*FIG. 3A*

(j) SEQ ID NO. 10
Dpta-R
TTACTGCTGCTGTGCAGACTGAATCGCAGTCAGCGCGATGGTGTAGACGATATCGTCAACCAGT
GCGCCACGGGACAGGTCATATGAATATCCTCCTTAG (k) SEQ ID NO. 11
Ack-U
ATTCATTGAGTCGTCAAATT (l) SEQ ID NO. 12
Ack-D
ATTGCGGACATAGCGCAAAT (m) SEG ID NO. 13
MgsA-1
GTACATTATGGAACTGACGACTCGCACTTTACCTGCGCGGTGTAGGCTGGAGCTGCTTCG (n) SEQ ID NO. 14
MgsA-2
CTTCAGACGGTCCGCGAGATAACGCTGATAATCGGGGATCCATATGAATATCCTCCTTAG (o) SEQ ID NO. 15
MgsA-3
CTTGAATTGTTGGATGGCGATG (p) SEG ID NO. 16
MgsA-4
CGTCACGTTATTGGATGAGAG (q) SEQ ID NO. 17
PpcR
TCGCATTGGCGCGAATATGCTCGGGCTTTGCTTTTCGTCAGTGGTTGAATTATTTGCTCAGGAT
GTGGCATTGTCAAGGGCATATGAATATCCTCCTTAG (r) SEQ ID NO. 18
PpcF
CGATTTTTTAACATTTCCATAAGTTACGCTTATTTAAAGCGTCGTGAATTTAATGACGTAAATT
CCTGCTATTTATTCGTGTGTAGGCTGGAGCTGCTTC

*FIG. 3B*

(s) SEQ ID NO. 19
1.6GI promoter
CGAGCCGTCACGCCCTTGACAATGCCACATCCTGAGCAAATAAT (t) SEQ ID NO. 20
Short 1.6 GI promoter
GCCCTTGACAATGCCACATCCTGAGCAAATAATTCAACCACT (u) SEQ ID NO. 22
Short 1.5 GI promoter
GCCCTTGACTATGCCACATCCTGAGCAAATAATTCAACCACT (v) SEQ ID NO. 23
GapA-R1
AGTCATATATTCCACCAGCTATTTGTTAGTGAATAAAAGTGGTTGAATTATTTGCTCAGGATGTG
GCATAGTCAAGGGCATATGAATATCCTCCTTAG (w) SEQ ID NO. 24
GapA-R2
GCTCACATTACGTGACTGATTCTAACAAAACATTAACACCAACTGGCAAAATTTTGTCCGTGTAG
GCTGGAGCTGCTTCG (x) SEQ ID NO. 25
GapA-R3
GTCGACAAACGCTGGTATACCTCA (y) SEQ ID NO. 26
GapA-R5
AGTCATATATTCCACCAGCTATTTGTTAGTGAATAAAAGTGGTTGAATTATTTGCTCAGGATGTG
GCATTGTCAAGGGCATATGAATATCCTCCTTAG

*FIG. 3C*

```
TAGTAAAGCCCTCGCTAGATTTTAATGCGGATGTTGCGATTACTTCGCCAACTATTGCGATAA
CAAGAAAAAGCCAGCCTTTCATGATATATCTCCCAATTTGTGTAGGGCTTATTATGCACGCTT
AAAAATAATAAAAGCAGACTTGACCTGATAGTTTGGCTGTGAGCAATTATGTGCTTAGTGCAT
CTAACGCTTGAGTTAAGCCGCGCCGCGAAGCGGCGTCGGCTTGAACGAATTGTTAGACATTAT
TTGCCGACTACCTTGGTGATCTCGCCTTTCACGTAGTGGACAAATTCTTCCAACTGATCTGCG
CGCGAGGCCAAGCGATCTTCTTCTTGTCCAAGATAAGCCTGTCTAGCTTCAAGTATGACGGGC
TGATACTGGGCCGGCAGGCGCTCCATTGCCCAGTCGGCAGCGACATCCTTCGGCGCGATTTTG
CCGGTTACTGCGCTGTACCAAATGCGGGACAACGTAAGCACTACATTTCGCTCATCGCCAGCC
CAGTCGGGCGGCGAGTTCCATAGCGTTAAGGTTTCATTTAGCGCCTCAAATAGATCCTGTTCA
GGAACCGGATCAAAGAGTTCCTCCGCCGCTGGACCTACCAAGGCAACGCTATGTTCTCTTGCT
TTTGTCAGCAAGATAGCCAGATCAATGTCGATCGTGGCTGGCTCGAAGATACCTGCAAGAATG
TCATTGCGCTGCCATTCTCCAAATTGCAGTTCGCGCTTAGCTGGATAACGCCACGGAATGATG
TCGTCGTGCACAACAATGGTGACTTCTACAGCGCGGAGAATCTCGCTCTCTCCAGGGGAAGCC
GAAGTTTCCAAAAGGTCGTTGATCAAAGCTCGCCGCGTTGTTTCATCAAGCCTTACGGTCACC
GTAACCAGCAAATCAATATCACTGTGTGGCTTCAGGCCGCCATCCACTGCGGAGCCGTACAAA
TGTACGGCCAGCAACGTCGGTTCGAGATGGCGCTCGATGACGCCAACTACCTCTGATAGTTGA
GTCGATACTTCGGCGATCACCGCTTCCCTCATGATGTTTAACTTTGTTTTAGGGCGACTGCCC
TGCTGCGTAACATCGTTGCTGCTCCATAACATCAAACATCGACCCACGGCGTAACGCGCTTGC
TGCTTGGATGCCCGAGGCATAGACTGTACCCCAAAAAAACAGTCATAACAAGCCATGAAAACC
GCCACTGCGCCGTTACCACCGCTGCGTTCGGTCAAGGTTCTGGACCAGTTGCGTGAGCGCATA
CGCTACTTGCATTACAGCTTACGAACCGAACAGGCTTATGTCCACTGGGTTCGTGCCTTCATC
CGTTTCCACGGTGTGCGTCACCCGGCAACCTTGGGCAGCAGCGAAGTCGAGGCATTTCTGTCC
TGGCTGGCGAACGAGCGCAAGGTTTCGGTCTCCACGCATCGTCAGGCATTGGCGGCCTTGCTG
TTCTTCTACGGCAAGGTGCTGTGCACGGATCTGCCCTGGCTTCAGGAGATCGGAAGACCTCGG
CCGTCGCGGCGCTTGCCGGTGGTGCTGACCCCGGATGAAGTGGTTCGCATCCTCGGTTTTCTG
GAAGGCGAGCATCGTTTGTTCGCCCAGCTTCTGTATGGAACGGGCATGCGGATCAGTGAGGGT
TTGCAACTGCGGGTCAAGGATCTGGATTTCGATCACGGCACGATCATCGTGCGGGAGGGCAAG
GGCTCCAAGGATCGGGCCTTGATGTTACCCGAGAGCTTGGCACCCAGCCTGCGCGAGCAGGGG
AATTAATTC
```

FIG. 6A

```
CCACGGGTTTTGCTGCCCGCAAACGGGCTGTTCTGGTGTTGCTAGTTTGTTATCAGAATCGCA
GATCCGGCTTCAGCCGGTTTGCCGGCTGAAAGCGCTATTTCTTCCAGAATTGCCATGATTTTT
TCCCCACGGGAGGCGTCACTGGCTCCCGTGTTGTCGGCAGCTTTGATTCGATAAGCAGCATCG
CCTGTTTCAGGCTGTCTATGTGTGACTGTTGAGCTGTAACAAGTTGTCTCAGGTGTTCAATTT
CATGTTCTAGTTGCTTTGTTTTACTGGTTTCACCTGTTCTATTAGGTGTTACATGCTGTTCAT
CTGTTACATTGTCGATCTGTTCATGGTGAACAGCTTTGAATGCACCAAAAACTCGTAAAAGCT
CTGATGTATCTATCTTTTTTACACCGTTTTCATCTGTGCATATGGACAGTTTTCCCTTTGATA
TGTAACGGTGAACAGTTGTTCTACTTTTGTTTGTTAGTCTTGATGCTTCACTGATAGATACAA
GAGCCATAAGAACCTCAGATCCTTCCGTATTTAGCCAGTATGTTCTCTAGTGTGGTTCGTTGT
TTTTGCGTGAGCCATGAGAACGAACCATTGAGATCATACTTACTTTGCATGTCACTCAAAAAT
TTTGCCTCAAAACTGGTGAGCTGAATTTTTGCAGTTAAAGCATCGTGTAGTGTTTTTCTTAGT
CCGTTATGTAGGTAGGAATCTGATGTAATGGTTGTTGGTATTTTGTCACCATTCATTTTTATC
TGGTTGTTCTCAAGTTCGGTTACGAGATCCATTTGTCTATCTAGTTCAACTTGGAAAATCAAC
GTATCAGTCGGGCGGCCTCGCTTATCAACCACCAATTTCATATTGCTGTAAGTGTTTAAATCT
TTACTTATTGGTTTCAAAACCCATTGGTTAAGCCTTTTAAACTCATGGTAGTTATTTTCAAGC
ATTAACATGAACTTAAATTCATCAAGGCTAATCTCTATATTTGCCTTGTGAGTTTTCTTTTGT
GTTAGTTCTTTTAATAACCACTCATAAATCCTCATAGAGTATTTGTTTTCAAAAGACTTAACA
TGTTCCAGATTATATTTTATGAATTTTTTTAACTGGAAAAGATAAGGCAATATCTCTTCACTA
AAAACTAATTCTAATTTTTCGCTTGAGAACTTGGCATAGTTTGTCCACTGGAAAATCTCAAAG
CCTTTAACCAAAGGATTCCTGATTTCCACAGTTCTCGTCATCAGCTCTCTGGTTGCTTTAGCT
AATACACCATAAGCATTTTCCCTACTGATGTTCATCATCTGAGCGTATTGGTTATAAGTGAAC
GATACCGTCCGTTCTTTCCTTGTAGGGTTTTCAATCGTGGGGTTGAGTAGTGCCACACAGCAT
AAAATTAGCTTGGTTTCATGCTCCGTTAAGTCATAGCGACTAATCGCTAGTTCATTTGCTTTG
AAAACAACTAATTCAGACATACATCTCAATTGGTCTAGGTGATTTTAATCACTATACCAATTG
AGATGGGCTAGTCAATGATAATTACTAGTCCTTTTCCTTTGAGTTGTGGGTATCTGTAAATTC
TGCTAGACCTTTGCTGGAAAACTTGTAAATTCTGCTAGACCCTCTGTAAATTCCGCTAGACCT
TTGTGTGTTTTTTTTGTTTATATTCAAGTGGTTATAATTTATAGAATAAAGAAAGAATAAAAA
AAGATAAAAGAATAGATCCCAGCCCTGTGTATAACTCACTACTTTAGTCAGTTCCGCAGTAT
TACAAAAGGATGTCGCAAACGCTGTTTGCTCCTCTACAAAACAGACCTTAAAACCCTA
```

FIG. 6B

```
AAGGCTTAAGTAGCACCCTCGCAAGCTCGGGCAAATCGCTGAATATTCCTTTTGTCTCCGACC
ATCAGGCACCTGAGTCGCTGTCTTTTTCGTGACATTCAGTTCGCTGCGCTCACGGCTCTGGCA
GTGAATGGGGGTAAATGGCACTACAGGCGCCTTTTATGGATTCATGCAAGGAAACTACCCATA
ATACAAGAAAAGCCCGTCACGGGCTTCTCAGGGCGTTTTATGGCGGGTCTGCTATGTGGTGCT
ATCTGACTTTTTGCTGTTCAGCAGTTCCTGCCCTCTGATTTTCCAGTCTGACCACTTCGGATT
ATCCCGTGACAGGTCATTCAGACTGGCTAATGCACCCAGTAAGGCAGCGGTATCATCAACAGG
CTTACCCGTCTTACTGTCGGGAATTCATTTAAATAGTCAAAAGCCTCCGACCGGAGGCTTTTG
ACTGCTAGGCGATCTGTGCTGTTTGCCACGGTATGCAGCACCAGCGCGAGATTATGGGCTCGC
ACGCTCGACTGTCGGACGGGGGCACTGGAACGAGAAGTCAGGCGAGCCGTCACGCCCTTGACA
ATGCCACATCCTGAGCAAATAATTCAACCACTAAACAAATCAACCGCGTTTCCCGGAGGTAAC
CAAGCTTGCGGGAGAGAATGATGAACAAGAGCCAACAAGTTCAGACAATCACCCTGGCCGCCG
CCCAGCAAATGGCGGCGGCGGTGGAAAAAAAGCCACTGAGATCAACGTGGCGGTGGTGTTTT
CCGTAGTTGACCGCGGAGGCAACACGCTGCTTATCCAGCGGATGGACGAGGCCTTCGTCTCCA
GCTGCGATATTTCCCTGAATAAAGCCTGGAGCGCCTGCAGCCTGAAGCAAGGTACCCATGAAA
TTACGTCAGCGGTCCAGCCAGGACAATCTCTGTACGGTCTGCAGCTAACCAACCAACAGCGAA
TTATTATTTTTGGCGGCGGCCTGCCAGTTATTTTTAATGAGCAGGTAATTGGCGCCGTCGGCG
TTAGCGGCGGTACGGTCGAGCAGGATCAATTATTAGCCCAGTGCGCCCTGGATTGTTTTTCCG
CATTATAACCTGAAGCGAGAAGGTATATTATGAGCTATCGTATGTTCCGCCAGGCATTCTGAG
TGTTAACGAGGGGACCGTCATGTCGCTTTCACCGCCAGGCGTACGCCTGTTTTACGATCCGCG
CGGGCACCATGCCGGCGCCATCAATGAGCTGTGCTGGGGGCTGGAGGAGCAGGGGGTCCCCTG
CCAGACCATAACCTATGACGGAGGCGGTGACGCCGCTGCGCTGGGCGCCCTGGCGGCCAGAAG
CTCGCCCCTGCGGGTGGGTATCGGCTCAGCGCGTCCGGCGAGATAGCCCTCACTCATGCCCA
GCTGCCGGCGGACGCGCCGCTGGCTACCGGACACGTCACCGATAGCGACGATCAACTGCGTAC
GCTCGGCGCCAACGCCGGGCAGCTGGTTAAAGTCCTGCCGTTAAGTGAGAGAAACTGAATGTA
TCGTATCTATACCCGCACCGGGGATAAAGGCACCACCGCCCTGTACGGCGGCAGCCGCATCGA
GAAAGACCATATTCGCGTCGAGGCCTACGGCACCGTCATGAACTGATATCCCAGCTGGGCGT
CTGCTACGCCACGACCCGCGACGCCGGGCTGCGGGAAAGCCTGCACCATATTCAGCAGACGCT
GTTCGTGCTGGGGGCTGAACTGGCCAGCGATGCGCGGGGCCTGACCCGCCTG
```

*FIG. 6C*

AGCCAGACGATCGGCGAAGAGGAGATCACCGCCCTGGAGCGGCTTATCGACCGCAATATGGCC
GAGAGCGGCCCGTTAAAACAGTTCGTGATCCCGGGGAGGAATCTCGCCTCTGCCCAGCTGCAC
GTGGCGCGCACCCAGTCCCGTCGGCTCGAACGCCTGCTGACGGCCATGGACCGCGCGCATCCG
CTGCGCGACGCGCTCAAACGCTACAGCAATCGCCTGTCGGATGCCCTGTTCTCCATGGCGCGA
ATCGAAGAGACTAGGCCTGATGCTTGCGCTTGAACTGGCCTAGCAAACACAGAAAAAAGCCCG
CACCTGACAGTGCGGGCTTTTTTTTTCCTAGGCGATCTGTGCTGTTTGCCACGGTATGCAGCA
CCAGCGCGAGATTATGGGCTCGCACGCTCGACTGTCGGACGGGGGCACTGGAACGAGAAGTCA
GGCGAGCCGTCACGCCCTTGACAATGCCACATCCTGAGCAAATAATTCAACCACTAAACAAAT
CAACCGCGTTTCCCGGAGGTAACCAAGCTTCACCTTTTGAGCCGATGAACAATGAAAAGATCA
AAACGATTTGCAGTACTGGCCCAGCGCCCCGTCAATCAGGACGGGCTGATTGGCGAGTGGCCT
GAAGAGGGGCTGATCGCCATGGACAGCCCCTTTGACCCGGTCTCTTCAGTAAAAGTGGACAAC
GGTCTGATCGTCGAACTGGACGGCAAACGCCGGGACCAGTTTGACATGATCGACCGATTTATC
GCCGATTACGCGATCAACGTTGAGCGCACAGAGCAGGCAATGCGCCTGGAGGCGGTGGAAATA
GCCCGTATGCTGGTGGATATTCACGTCAGCCGGGAGGAGATCATTGCCATCACTACCGCCATC
ACGCCGGCCAAAGCGGTCGAGGTGATGGCGCAGATGAACGTGGTGGAGATGATGATGGCGCTG
CAGAAGATGCGTGCCCGCCGGACCCCCTCCAACCAGTGCCACGTCACCAATCTCAAAGATAAT
CCGGTGCAGATTGCCGCTGACGCCGCCGAGGCCGGGATCCGCGGCTTCTCAGAACAGGAGACC
ACGGTCGGTATCGCGCGCTACGCGCCGTTTAACGCCCTGGCGCTGTTGGTCGGTTCGCAGTGC
GGCCGCCCCGGCGTGTTGACGCAGTGCTCGGTGGAAGAGGCCACCGAGCTGGAGCTGGGCATG
CGTGGCTTAACCAGCTACGCCGAGACGGTGTCGGTCTACGGCACCGAAGCGGTATTTACCGAC
GGCGATGATACGCCGTGGTCAAAGGCGTTCCTCGCCTCGGCCTACGCCTCCCGCGGGTTGAAA
ATGCGCTACACCTCCGGCACCGGATCCGAAGCGCTGATGGGCTATTCGGAGAGCAAGTCGATG
CTCTACCTCGAATCGCGCTGCATCTTCATTACTAAAGGCGCCGGGGTTCAGGGACTGCAAAAC
GGCGCGGTGAGCTGTATCGGCATGACCGGCGCTGTGCCGTCGGGCATTCGGGCGGTGCTGGCG
GAAAACCTGATCGCCTCTATGCTCGACCTCGAAGTGGCGTCCGCCAACGACCAGACTTTCTCC
CACTCGGATATTCGCCGCACCGCGCGCACCCTGATGCAGATGCTGCCGGGCACCGACTTTATT
TTCTCCGGCTACAGCGCGGTGCCGAACTACGACAACATGTTCGCCGGCTCGAACTTCGATGCG
GAAGATTTTGATGATTACAACATCCTGCAGCGTGACCTGATGGTTG

FIG. 6D

```
ACGGCGGCCTGCGTCCGGTGACCGAGGCGGAAACCATTGCCATTCGCCAGAAAGCGGCGCGGG
CGATCCAGGCGGTTTTCCGCGAGCTGGGGCTGCCGCCAATCGCCGACGAGGAGGTGGAGGCCG
CCACCTACGCGCACGGCAGCAACGAGATGCCGCCGCGTAACGTGGTGGAGGATCTGAGTGCGG
TGGAAGAGATGATGAAGCGCAACATCACCGGCCTCGATATTGTCGGCGCGCTGAGCCGCAGCG
GCTTTGAGGATATCGCCAGCAATATTCTCAATATGCTGCGCCAGCGGGTCACCGGCGATTACC
TGCAGACCTCGGCCATTCTCGATCGGCAGTTCGAGGTGGTGAGTGCGGTCAACGACATCAATG
ACTATCAGGGGCCGGGCACCGGCTATCGCATCTCTGCCGAACGCTGGGCGGAGATCAAAAATA
TTCCGGGCGTGGTTCAGCCCGACACCATTGAATAAGGCGGTATTCCTGTGCAACAGACAACCC
AAATTCAGCCCTCTTTTACCCTGAAAACCCGCGAGGGCGGGGTAGCTTCTGCCGATGAACGCG
CCGATGAAGTGGTGATCGGCGTCGGCCCTGCCTTCGATAAACACCAGCATCACACTCTGATCG
ATATGCCCCATGGCGCGATCCTCAAAGAGCTGATTGCCGGGGTGGAAGAAGAGGGGCTTCACG
CCCGGGTGGTGCGCATTCTGCGCACGTCCGACGTCTCCTTTATGGCCTGGGATGCGGCCAACC
TGAGCGGCTCGGGGATCGGCATCGGTATCCAGTCGAAGGGGACCACGGTCATCCATCAGCGCG
ATCTGCTGCCGCTCAGCAACCTGGAGCTGTTCTCCCAGGCGCCGCTGCTGACGCTGGAGACCT
ACCGGCAGATTGGCAAAAACGCTGCGCGCTATGCGCGCAAAGAGTCACCTTCGCCGGTGCCGG
TGGTGAACGATCAGATGGTGCGGCCGAAATTTATGGCCAAAGCCGCGCTATTTCATATCAAAG
AGACCAAACATGTGGTGCAGGACGCCGAGCCCGTCACCCTGCACATCGACTTAGTAAGGGAGT
GACCATGAGCGAGAAAACCATGCGCGTGCAGGATTATCCGTTAGCCACCCGCTGCCCGGAGCA
TATCCTGACGCCTACCGGCAAACCATTGACCGATATTACCCTCGAGAAGGTGCTCTCTGGCGA
GGTGGGCCCGCAGGATGTGCGGATCTCCCGCCAGACCCTTGAGTACCAGGCGCAGATTGCCGA
GCAGATGCAGCGCCATGCGGTGGCGCGCAATTTCCGCCGCGCGGCGGAGCTTATCGCCATTCC
TGACGAGCGCATTCTGGCTATCTATAACGCGCTGCGCCCGTTCCGCTCCTCGCAGGCGGAGCT
GCTGGCGATCGCCGACGAGCTGGAGCACACCTGGCATGCGACAGTGAATGCCGCCTTTGTCCG
GGAGTCGGCGGAAGTGTATCAGCAGCGGCATAAGCTGCGTAAAGGAAGCTAAGCGGAGGTCAG
CATGCCGTTAATAGCCGGGATTGATATCGGCAACGCCACCACCGAGGTGGCGCTGGCGTCCGA
CTACCCGCAGGCGAGGGCGTTTGTTGCCAGCGGGATCGTCGCGACGACGGGCATGAAAGGGAC
GCGGGACAATATCGCCGGGACCCTCGCCGCGCTGGAGCAGGCCCTGGCGAAAACACCGTGGTC
GATGAGCGATGTCTCTCGCATCTATCTTAACGAAGCCGCGCC
```

FIG. 6E

```
GGTGATTGGCGATGTGGCGATGGAGACCATCACCGAGACCATTATCACCGAATCGACCATGAT
CGGTCATAACCCGCAGACGCCGGGCGGGGTGGGCGTTGGCGTGGGGACGACTATCGCCCTCGG
GCGGCTGGCGACGCTGCCGGCGGCGCAGTATGCCGAGGGGTGGATCGTACTGATTGACGACGC
CGTCGATTTCCTTGACGCCGTGTGGTGGCTCAATGAGGCGCTCGACCGGGGGATCAACGTGGT
GGCGGCGATCCTCAAAAAGGACGACGGCGTGCTGGTGAACAACCGCCTGCGTAAAACCCTGCC
GGTGGTGGATGAAGTGACGCTGCTGGAGCAGGTCCCCGAGGGGGTAATGGCGGCGGTGGAAGT
GGCCGCGCCGGGCCAGGTGGTGCGGATCCTGTCGAATCCCTACGGGATCGCCACCTTCTTCGG
GCTAAGCCCGGAAGAGACCCAGGCCATCGTCCCCATCGCCCGCGCCCTGATTGGCAACCGTTC
CGCGGTGGTGCTCAAGACCCCGCAGGGGGATGTGCAGTCGCGGGTGATCCCGGCGGGCAACCT
CTACATTAGCGGCGAAAAGCGCCGCGGAGAGGCCGATGTCGCCGAGGGCGCGGAAGCCATCAT
GCAGGCGATGAGCGCCTGCGCTCCGGTACGCGACATCCGCGGCGAACCGGGCACCCACGCCGG
CGGCATGCTTGAGCGGGTGCGCAAGGTAATGGCGTCCCTGACCGGCCATGAGATGAGCGCGAT
ATACATCCAGGATCTGCTGGCGGTGGATACGTTTATTCCGCGCAAGGTGCAGGGCGGGATGGC
CGGCGAGTGCGCCATGGAGAATGCCGTCGGGATGGCGGCGATGGTGAAAGCGGATCGTCTGCA
AATGCAGGTTATCGCCCGCGAACTGAGCGCCCGACTGCAGACCGAGGTGGTGGTGGGCGGCGT
GGAGGCCAACATGGCCATCGCCGGGGCGTTAACCACTCCCGGCTGTGCGGCGCCGCTGGCGAT
CCTCGACCTCGGCGCCGGCTCGACGGATGCGGCGATCGTCAACGCGGAGGGGCAGATAACGGC
GGTCCATCTCGCCGGGGCGGGGAATATGGTCAGCCTGTTGATTAAAACCGAGCTGGGCCTCGA
GGATCTTTCGCTGGCGGAAGCGATAAAAAAATACCCGCTGGCCAAAGTGGAAAGCCTGTTCAG
TATTCGTCACGAGAATGGCGCGGTGGAGTTCTTTCGGGAAGCCCTCAGCCCGGCGGTGTTCGC
CAAAGTGGTGTACATCAAGGAGGGCGAACTGGTGCCGATCGATAACGCCAGCCCGCTGGAAAA
AATTCGTCTCGTGCGCCGGCAGGCGAAAGAGAAAGTGTTTGTCACCAACTGCCTGCGCGCGCT
GCGCCAGGTCTCACCCGGCGGTTCCATTCGCGATATCGCCTTTGTGGTGCTGGTGGGCGGCTC
ATCGCTGGACTTTGAGATCCCGCAGCTTATCACGGAAGCCTTGTCGCACTATGGCGTGGTCGC
CGGGCAGGGCAATATTCGGGAACAGAAGGGCCGCGCAATGCGGTCGCCACCGGGCTGCTACT
GGCCGGTCAGGCGAATTAAACGGGCGCTCGCGCCAGCCTCTAGGTACAAATAAAAAGGCACG
TCAGATGACGTGCCTTTTTTCTTGTCTAGAGTACTGGCGAAAGGGGGATGTGCTGCAAGGCGA
TTAAGTTGGGTAACGCCAGGGTTTTCCCAGTC
```

FIG. 6F

ACGACGTTGTAAAACGACGGCCAGTGAATTCGAGCTCGGTACCCGGGGCGGCCGCGCTAGCGC
CCGATCCAGCTGGAGTTTGTAGAAACGCAAAAAGGCCATCCGTCAGGATGGCCTTCTGCTTAA
TTTGATGCCTGGCAGTTTATGGCGGGCGTCCTGCCCGCCACCCTCCGGGCCGTTGCTTCGCAA
CGTTCAAATCCGCTCCCGGCGGATTTGTCCTACTCAGGAGAGCGTTCACCGACAAACAACAGA
TAAAACGAAAGGCCCAGTCTTTCGACTGAGCCTTTCGTTTTATTTGATGCCTGGCAGTTCCCT
ACTCTCGCATGGGGAGACCCCACACTACCATCGGCGCTACGGCGTTTCACTTCTGAGTTCGGC
ATGGGGTCAGGTGGGACCACCGCGCTACTGCCGCCAGGCAAATTCTGTTTTATCAGACCGCTT
CTGCGTTCTGATTTAATCTGTATCAGGCTGAAAATCTTCTCTCATCCGCCAAAACAGCCAAGC
TTGCATGCCTGCAGCCCGGGTTACCATTTCAACAGATCGTCCTTAGCATATAAGTAGTCGTCA
AAAATGAATTCAACTTCGTCTGTTTCGGCATTGTAGCCGCCAACTCTGATGGATTCGTGGTTT
TTGACAATGATGTCACAGCCTTTTTCCTTTAGGAAGTCCAAGTCGAAAGTAGTGGCAATACCA
ATGATCTTACAACCGGCGGCTTTTCCGGCGGCAATACCTGCTGGAGCGTCTTCAAATACTACT
ACCTTAGATTTGGAAGGGTCTTGCTCATTGATCGGATATCCTAAGCCATTCCTGCCCTTCAGA
TATGGTTCTGGATGAGGCTTACCCTGTTTGACATCATTAGCGGTAATGAAGTACTTTGGTCTC
CTGATTCCCAGATGCTCGAACCATTTTTGTGCCATATCACGGGTACCGGAAGTTGCCACAGCC
CATTTCTCTTTTGGTAGAGCGTTCAAAGCGTTGCACAGCTTAACTGCACCTGGGACTTCAATG
GATTTTTCACCGTACTTGACCGGAATTTCAGCTTCTAATTTGTTAACATACTCTTCATTGGCA
AAGTCTGGAGCGAACTTAGCAATGGCATCAAACGTTCTCCAACCATGCGAGACTTGGATAACG
TGTTCAGCATCGAAATAAGGTTTGTCCTTACCGAAATCCCTCCAGAATGCAGCAATGGCTGGT
TGAGAGATGATAATGGTACCGTCGACGTCGAACAAAGCGGCGTTAACTTTCAAAGATAGAGGT
TTAGTAGTCAATCCCATAATTCTAGTCTGTTTCCTGGATCCAATAAATCTAATCTTCATGTAG
ATCTAATTCTTCAATCATGTCCGGCAGGTTCTTCATTGGGTAGTTGTTGTAAACGATTTGGTA
TACGGCTTCAAATAATGGGAAGTCTTCGACAGAGCCACATGTTTCCAACCATTCGTGAACTTC
TTTGCAGGTAATTAAACCTTGAGCGGATTGGCCATTCAACAACTCCTTTTCACATTCCCAGGC
GTCCTTACCAGAAGTAGCCATTAGCCTAGCAACCTTGACGTTTCTACCACCAGCGCAGGTGGT
GATCAAATCAGCAACACCAGCAGACTCTTGGTAGTATGTTTCTTCTCTAGATTCTGGGAAAAA
CATTTGACCGAATCTGATGATCTCACCCAAACCGACTCTTTGGATGGCAGCAGAAGCGTTGTT
ACCCCAGCCTAGACCTTCGACGAAACCACAACCTAAGGCAACAACGTTCTTCAAAGCACCACA
GATGGAGATACCAGCAACATCTTCG

FIG. 6G

ATGACACTAACGTGGAAGTAAGGTCTGTGGAACAAGGCCTTTAGAACCTTATGGTCGACGTCC
TTGCCCTCGCCTCTGAAATCCTTTGGAATGTGGTAAGCAACTGTTGTTTCAGACCAGTGTTCT
TGAGCGACTTCGGTGGCAATGTTAGCACCAGATAGAGCACCACATTGAATACCTAGTTCCTCA
GTGATGTAAGAGGATAGCAATTGGACACCTTTAGCACCAACTTCAAAACCCTTTAGACAGGAG
ATAGCTCTGACGTGTGAATCAACATGACCTTTCAATTGGCTACAGATACGGGCAAAAATTGA
TGTGGAATGTTGAAAACGATGATGTCGACATCCTTGACTGAATCAATCAAGTCTGGATTAGCA
ACCAAATTGTCGGGTAGAGTGATGCCAGGCAAGTATTTCACGTTTTGATGTCTAGTATTTATG
ATTTCAGTCAATTTTTCACCATTGATCTCTTCTTCGAACACCCACATTTGTACTATTGGAGCG
AAAACTTCTGGGTATCCCTTACAATTTTCGGCAACCACCTTGGCAATAGTAGTACCCCAGTTA
CCAGATCCAATCACAGTAACCTTGAAAGGCTTTTCGGCAGCCTTCAAAGAAACAGAAGAGGAA
CTTCTCTTTCTACCAGCATTCAAGTGGCCGGAAGTTAAGTTTAATCTATCAGCAGCAGCAGCC
ATGGAATTGTCCTCCTTACTAGTCATGGTCTGTTTCCTGTGTGAAATTGTTATCCGCTCACAA
TTCCACACATTATACGAGCCGGATGATTAATTGTCAACAGCTCATTTCAGAATATTTGCCAGA
ACCGTTATGATGTCGGCGCAAAAAACATTATCCAGAACGGGAGTGCGCCTTGAGCGACACGAA
TTATGCAGTGATTTACGACCTGCACAGCCATACCACAGCTTCCGATGGCTGCCTGACGCCAGA
AGCATTGGTGCACGCTAGCCAGTACATTTAAATGGTACCCTCTAGTCAAGGCCTTAAGTGAGT
CGTATTACGGACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGCGCCTGATGCGGTATTTTCTCC
TTACGCATCTGTGCGGTATTTCACACCGCATATGGTGCACTCTCAGTACAATCTGCTCTGATG
CCGCATAGTTAAGCCAGCCCCGACACCCGCCAACACCCGCTGACGAGCT
```

FIG. 6H

PRODUCTION OF BACTERIAL STRAINS

CROSS REFERENCE TO RELATED APPLICATIONS

This application is a Continuation of U.S. application Ser. No. 10/527,827, filed Dec. 14, 2005, which is a 371 National Phase Application of PCT/US03/31445, filed Oct. 3, 2003, which claims priority to U.S. Provisional Application 60/416,167 and 60/416,192, both filed Oct. 4, 2002 all of which are hereby incorporated by reference.

FIELD OF THE INVENTION

The present invention relates to alteration of metabolic pathways in bacterial strains and particularly in E. coli. More specifically the invention pertains to manipulating global regulatory genes, such as arcA and rpoS in bacterial host cells to enhance the production of desired products.

BACKGROUND OF THE INVENTION

Production of chemicals through cultivation of microorganisms is generally performed under well-controlled conditions wherein a constant environment regarding temperature, oxygen concentration and pH are maintained. In addition, culture vessels, which include the microorganisms, are fed with different types of nutrients that cells use for growth and the production of desired chemical compounds. Under these controlled conditions, certain metabolic pathways and physiological responses programmed into a cell's genome are unnecessary, and in fact, may interfere with the optimized performance of a preferred process. In bacterial cells a number of reactions in these metabolic pathways and physiological responses can be eliminated or enhanced to improve the production of desired products.

FIG. 1 illustrates a number of pathways and reactions involved in the assimilation of glucose. Enhanced efficient glucose assimilation can result in increased energy production, such as ATP, NADH, NADPH and FADH, for use by a bacterial strain. The increased energy production can then result in an increase in production and/or growth per unit weight of generating biomass or per unit weight of provided carbon substrate.

Generally, increased glucose assimilation and metabolite production in microorganisms by genetic engineering has involved inactivation or deregulation of specific enzymes; overexpression of genes that are involved in central metabolic routes, such as glycolysis and the TCA cycle; the introduction of heterologous genes; and various other approaches. However, microbial strains regulate their physiology not just by controlling specific steps in a pathway, but also by coordinating a number of biosynthetic and catabolic pathways through the use of global regulators. One of these global regulatory systems is the ArcB/ArcA regulatory system. Another global regulatory system is the RpoS system.

In particular, in facultative anaerobic bacteria, such as E. coli, some of the enzymes of the tricarboxylic acid (TCA) cycle are repressed under anaerobic conditions and particularly when the microorganisms are grown on glucose. The response of the TCA cycle enzymes in the absence to oxygen is regulated mainly at the transcriptional level by the ArcB/ArcA two-component regulatory system (NCBI entries NP 418818 (AE000400) and NP 417677 (AE000510)). ArcB (histidine kinase) senses the absence of oxygen and subsequently phosphorylates the regulator ArcA. The phosphorylated-ArcA then binds to regulatory regions, which are operably linked to the coding regions of TCA cycle regulated enzymes and either activates or represses transcription. Examples of enzymes regulated in this manner include succinate dehydrogenase, 2-oxoglutarate dehydrogenase, isocitrate dehydrogenase, and citrate synthase, which are all repressed by phosphorylated ArcA. (Lynch et al., (1996) in REGULATION OF GENE EXPRESSION IN ESCHERICHIA COLI. Eds. Lin et al., Chapman and Hall, New York). In arcA mutants, TCA cycle genes that were repressed by arcA become derepressed. (Iuchi et al., (1988) *PNAS USA* 85:1888-1892). Prohl et al. compared the production of products and specific enzyme activities in an E. coli wild-type strain and an E. coli arcA mutant strain, wherein the arcA was inactivated when the strains were grown on glucose or glycerol in the presence of oxygen or nitrate. (Prohl et al., (1998) *Arch. Microbiol.* 170: 1-7). The authors concluded that the strong repression of the TCA cycle during nitrate respiration (anaerobic conditions) occurs only during growth on glucose but not on other substrates, such as glycerol. However, deletion of arcA did not have any affect on E. coli strains when grown under aerobic conditions.

RpoS genes encode DNA-dependent RNA polymerase sigma subunits and when bound to the core RNA polymerase, allows the transcription of a subset of genes. For example in E. coli, rpoS is induced under various stress conditions and controls the expression of a catalase gene (katE) and glycogen biosynthesis. RpoS is believed to be a global regulator of the general stress response in bacteria and can be triggered by many different stress signals. Often, activation of rpoS is accompanied by a reduction or cessation of bacterial growth. This mechanism provides the host microorganism with the ability to survive the encountered stress as well as potential other stresses. (Hengge-Aronis, R. (2002) *Microbiol. Mol. Biol. Rev.* 66:373-395).

The major function of the general stress response is preventive. There are more than 70 rpoS dependent genes known and the majority of these confer resistance against oxidative stress, near-UV radiation, potentially lethal heat shock, hyperosmolarity, acidic pH and organic solvents. Compared with wild-type rpoS strains, rpoS mutants were unable able to induce the general stress response in bacteria and could not survive prolonged starvation periods (Hengge-Aronis R. (2002) *Microbiol. Mol. Biol. Rev.* 66:373-395). In recombinant bacterial strains, the production of protein during culture, and particularly during late stage fed-batch fermentation, may result in a general stressful condition, which may induce the RpoS-dependent response. It has been demonstrated that in continuous culture, at low dilution rates of, for example 0.13 h$^{-1}$, a rpoS$^-$ strain produced more recombinant protein than the wild-type strain. However, the effect was promoter dependent, and at higher dilution rates (0.38 h$^{-1}$) the mutation had no effect on the production of recombinant protein. (Chou et al., (1996) *Biotechnol. Bioeng.* 50:636-642). It is believed the effect of a rpoS mutation on the production of metabolites has not been reported.

The phosphoenolpyruvate carboxylase (Ppc) enzyme (E.C. 4.1.1.31/32/38/49) catalyzes the conversion of phosphoenolpyruvate (PEP) to oxaloacetate (OAA). Ppc replenishes the TCA cycle by directly providing OAA, which may have been removed for other biosynthetic reactions. If OAA is not replenished, the efficiency of the TCA cycle may be diminished. E. Coli cells having an inactivated ppc (ppc$^-$) grew slower than wild-type ppc$^-$ cells (ppc$^+$), and the ppc$^+$ cells used glucose about three times as efficiently as the ppc$^-$ cells. However, despite this effect, the ppc$^-$ cells overproduced phenylalanine (Phe). The ppc$^-$ cells produced at least 16 times more Phe than the ppc$^+$ cells. The production of unwanted by-products, such as acetate and pyruvate were also stimulated in the ppc⁻ cells. (Miller et al., (1987) *Microbiol.* 2:143-149). In another study the overproduction of Ppc in *E. coli* was effected by cloning the ppc in a multicopy plasmid under a tac promoter resulting in an increase in growth yield on glucose as well a decrease in the secretion of organic acids. (Liao et al., (1993) *Appl. Environ. Microbiol.* 59:4261-4265). The above results suggest that the wild-type level of Ppc is not optimal for the most efficient glucose utilization in batch cultures. Overexpression of Ppc is expected to favor the production of amino acids of the OAA family, such as Asp, Met, Lys, Thr and Ile.

By modification of a global regulator such as arcA or rpoS and optionally by overexpression of ppc, a more efficient metabolic pathway for glucose assimilation may be achieved in a bacterial microorganism.

BRIEF SUMMARY OF THE INVENTION

In one embodiment, the invention provides a genetically engineered microorganism comprising an inactivated endogenous global regulator selected from the group of arcA genes or rpoS genes and optionally an exogenous promoter operably linked to a polynucleotide encoding a protein having phosphoenolpyruvate (PEP) carboxylase activity, wherein the engineered microorganism is capable of enhanced production of biomaterials, enhanced cell growth and/or enhanced cell productivity. The genetically modified microorganism encompassed by the invention may further include inactivation of i) an endogenous gene encoding a protein having phosphogluconate dehydratase (Edd) activity, ii) an endogenous gene encoding a protein having phosphoacetylkinase (Pta) activity, iii) an endogenous gene encoding a protein having acetate kinase (AckA) activity and/or iv) an endogenous gene encoding a protein having methygloxyal synthase (MgsA) activity.

One aspect of the invention pertains to a method of enhancing the production of a desired product in a bacterial host cell which comprises modifying a bacterial host cell by inactivating an endogenous arcA gene and culturing the modified bacterial host cell in suitable culture media comprising glucose under aerobic conditions to allow production of a desired product. In one embodiment, the bacterial host cell is from a strain of the Enterobacteriaceae family. Preferably the host cell is an *E. coli* or *Pantoea* cell, and preferably the host cell is a PTS⁻/Glu⁺ cell. In a second embodiment of this aspect, the desired product is glycerol, PEP, pyruvate, chorismate, ethanol, succinate or dihydroxyacetone-P. Preferably, the desired product is chorismate. According to the method of this aspect, the chorismate may be further converted to an aromatic amino acid. In a third embodiment of this aspect, the method further comprises inactivating the expression of an endogenous gene encoding a polypeptide having RpoS activity, Edd activity, Pta activity, AckA activity or MgsA activity. In a fourth embodiment of this aspect, the method further comprises transforming the bacterial host cell with a DNA fragment comprising an exogenous promoter, wherein the DNA fragment including the exogenous promoter is integrated into the host cell chromosome and replaces the endogenous promoter which is operably linked to a PEP carboxylase coding sequence wherein PEP carboxylase is overexpressed. In a fifth embodiment, the method further comprises isolating the desired product from the culture media.

A second aspect the invention pertains to a method of enhancing biomass production in bacterial host cells comprising modifying a bacterial host cell by inactivating an endogenous arcA gene and culturing the modified bacterial cell under suitable culture conditions wherein said culture conditions include aerobic fermentation and glucose as a carbon source and wherein biomass production is enhanced in the modified bacterial cell compared to biomass production in a corresponding non-modified bacterial cell cultured under essentially the same conditions. In one embodiment of the method according to this aspect further comprises inactivating an endogenous rpoS gene. In a second embodiment the endogenous arcA gene is inactivated by a deletion. In a third embodiment, the method further comprises inactivating an endogenous gene encoding a polypeptide having phosphogluconate dehydratase activity, phosphotransacetylase activity, acetyl kinase activity or methylglyoxyal synthase activity. Preferably the endogenous gene encoding a polypeptide having phosphogluconate dehydratase activity is an edd gene; the endogenous gene encoding a polypeptide having phosphotransacetylase activity is a pta gene; the endogenous gene encoding a polypeptide having acetyl kinase activity is an ackA gene; and the endogenous gene encoding a polypeptide having methylglyoxyal synthase activity is a mgsA gene. In a fourth embodiment the method further comprises isolating the modified bacterial cell. Preferred host cell according to this aspect are *Escherichia* cells, *Pantoea* cells, *Klebsiella* cells, *Gluconobacter* cells and *Erwinia* cells and most preferably *E. coli* cells and *Pantoea* cells.

A third aspect of the invention pertains to the modified bacterial cells obtained according to the method of aspect one or two.

In a fourth aspect the invention pertains to genetically engineered bacterial strains of the Enterobacteriacea family comprising an inactivated endogenous arcA gene and an overexpressed polypeptide having PEP carboxylase activity. Preferably the bacterial strain is an *Escherichia, Pantoea, Klebsiella, Gluconobacter* or *Erwinia* strain and particularly a strain *E. coli*. In a further embodiment, the endogenous arcA gene is deleted. In yet another embodiment the engineered bacterial strain will comprise an inactivated endogenous mgsA; an inactivated endogenous edd; and/or an inactivated endogenous rpoS. In one preferred embodiment, the engineered bacterial strain will include an overexpressed polypeptide having PEP carboxylase which is operably linked to an exogenous promoter. In a preferred embodiment the exogenous promoter is a GI promoter.

In a fifth aspect the invention pertains to a genetically engineered bacterial strain comprising an inactivated endogenous rpoS gene. In one embodiment the endogenous rpoS gene is deleted. In another embodiment the engineered strain further comprises an overexpressed polypeptide having PEP carboxylase activity. In yet another embodiment, the engineered bacterial strain has a PTS⁻/Glu⁺ phenotype, which was derived from a bacterial strain originally capable of utilizing a PTS for carbohydrate transport. Preferably the bacterial strain is *E. coli* strain.

In a sixth aspect the invention pertains to a method of enhancing the production of an aromatic amino acid in an *E. coli* host cell comprising, modifying an *E. coli* host cell by inactivating an endogenous arcA gene and culturing the modified host cell in suitable culture media comprising glucose under aerobic conditions to allow production of an aromatic amino acid. In a preferred embodiment the *E. coli* host cell is a PTS⁻/Glu⁺ cell. In another embodiment the endogenous arcA gene is inactivated by a deletion. In a further embodiment the invention relates to the modified *E. coli* host cell obtained according to the method of this aspect.

The numbers represent key reactions in glucose assimilation. Reactions 1-3 comprise the most efficient pathway for glucose assimilation. Reaction 4 is the sum of reactions 1-4. Reaction 5-8 are alternative routes in glucose assimilation and these routes are in general either less efficient in the assimilation of glucose as compared to routes 1-3 or bypass the formation of important metabolic intermediates.

Figure 1A:
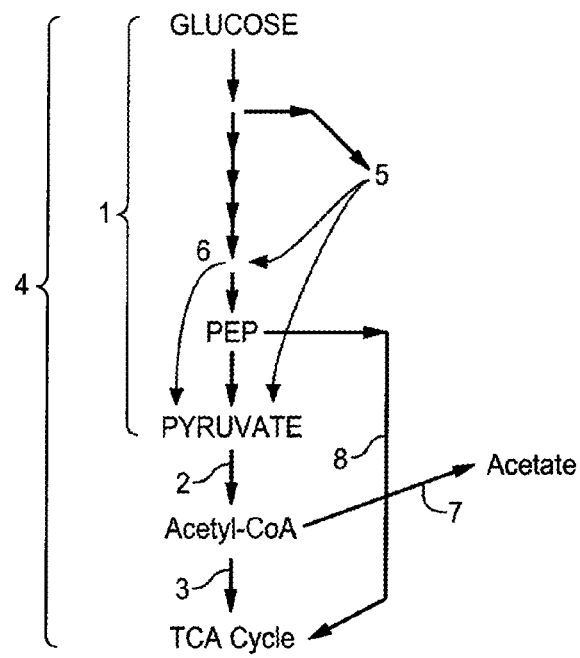
FIG. 1A is a schematic representation of interconnected metabolic routes, which are involved in glucose assimilation.

FIG. 1B further illustrates the numbered reactions of FIG. 1A and include glycolysis (reaction 1) and the Entner-Doudoroff pathway (reaction 5).

Figure 2:
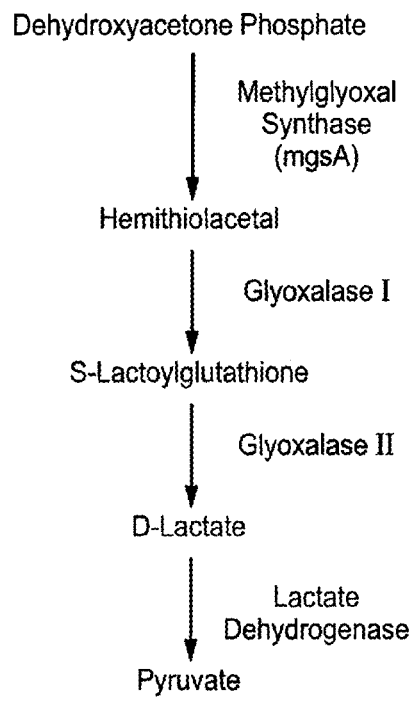

FIG. 2 depicts a general scheme for the synthesis and detoxification of methylglyoxal (encoded by mgsA) in E. coli.

FIG. 3 sets forth the nucleotide sequences (SEQ ID NOs. 1-18) of oligonucleotide primers used to either construct gene disruption or to confirm gene disruption as further discussed in the examples, wherein SEQ ID NO. 1 is the nucleotide sequence of ArcA1;
SEQ ID NO. 2 is the nucleotide sequence of ArcA2;
SEQ ID NO. 3 is the nucleotide sequence of ArcA3;
SEQ ID NO. 4 is the nucleotide sequence of ArcA4;
SEQ ID NO. 5 is the nucleotide sequence of Edd1;
SEQ ID NO. 6 is the nucleotide sequence of Edd2;
SEQ ID NO. 7 is the nucleotide sequence of Edd3;
SEQ ID NO. 8 is the nucleotide sequence of Edd4;
SEQ ID NO. 9 is the nucleotide sequence of DackA-F;
SEQ ID NO. 10 is the nucleotide sequence of DptaR;
SEQ ID NO. 11 is the nucleotide sequence of AckU;
SEQ ID NO. 12 is the nucleotide sequence of AckD;
SEQ ID NO. 13 is the nucleotide sequence of MgsA1;
SEQ ID NO. 14 is the nucleotide sequence of MgsA2;
SEQ ID NO. 15 is the nucleotide sequence of MgsA3;
SEQ ID NO. 16 is the nucleotide sequence of MgsA4;
SEQ ID NO. 17 is the nucleotide sequence of PpcR;
SEQ ID NO. 18 is the nucleotide sequence of PpcF;
SEQ ID NO. 19 is the nucleotide sequence of the 1.6 GI promoter;
SEQ ID NO. 20 is the nucleotide sequence of the short 1.6GI promoter;
SEQ ID NO. 22 is the nucleotide sequence of the 1.5 GI promoter;
SEQ ID NO. 23 is the nucleotide sequence of the primer, gapA-R2;
SEQ ID NO. 24 is the nucleotide sequence of the primer, gapA-R2;
SEQ ID NO. 25 is the nucleotide sequence of the primer, gapA-R3; and
SEQ ID NO. 26 is the nucleotide sequence of the primer, gapA-R5.

Figure 4A:
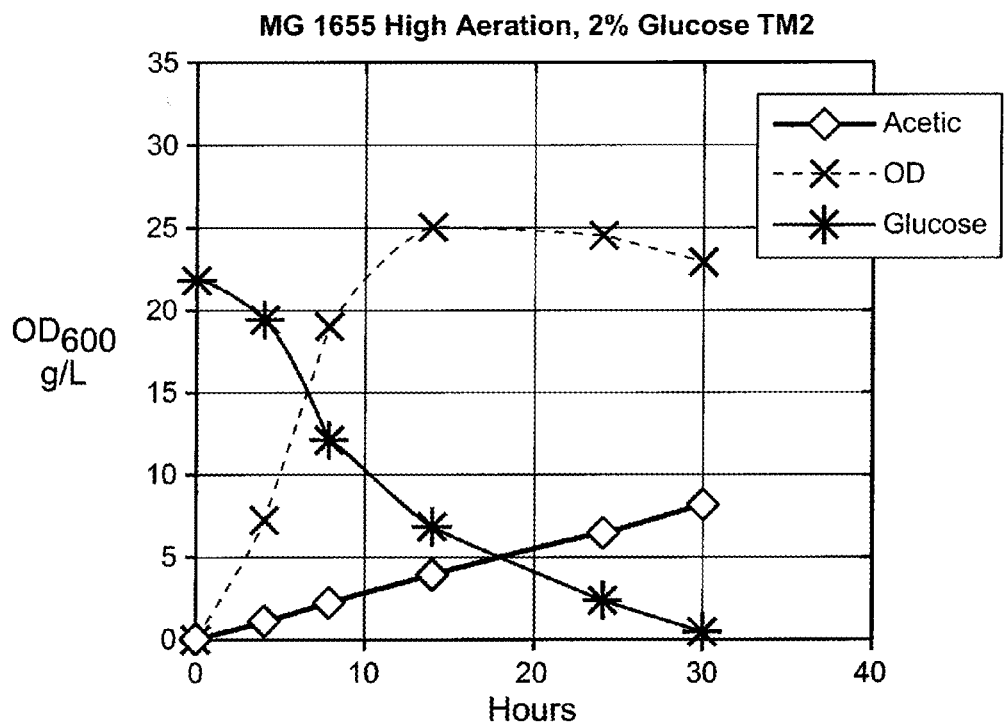

FIG. 4A refers to example 1 and illustrates the change in optical density ($OD_{600}$), glucose concentration (g/L) and acetate concentration (g/L) in a wild-type E. coli strain MG1655 grown in TM2 media over time (hrs).

Figure 4B:
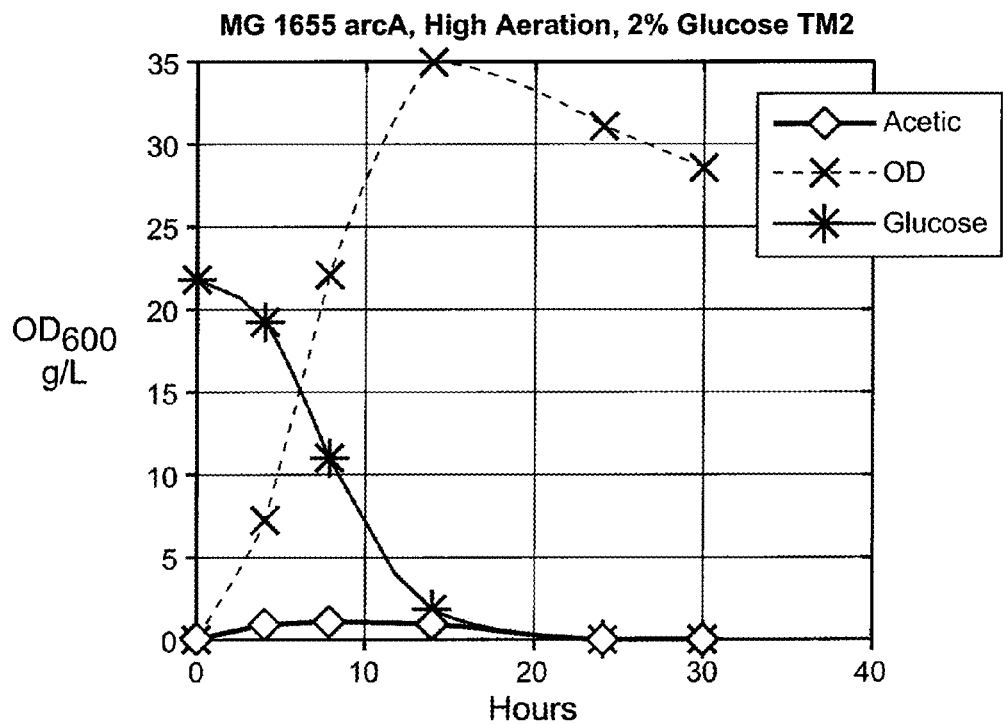

FIG. 4B illustrates the change in optical density ($OD_{600}$), glucose concentration (g/L) and acetate concentration (g/L) in a wild-type E. coli strain MG1655 arcA$^-$ strain ($\Delta$arcA) grown in TM2 media over time (hrs) as more fully described in example 1.

Figure 5:
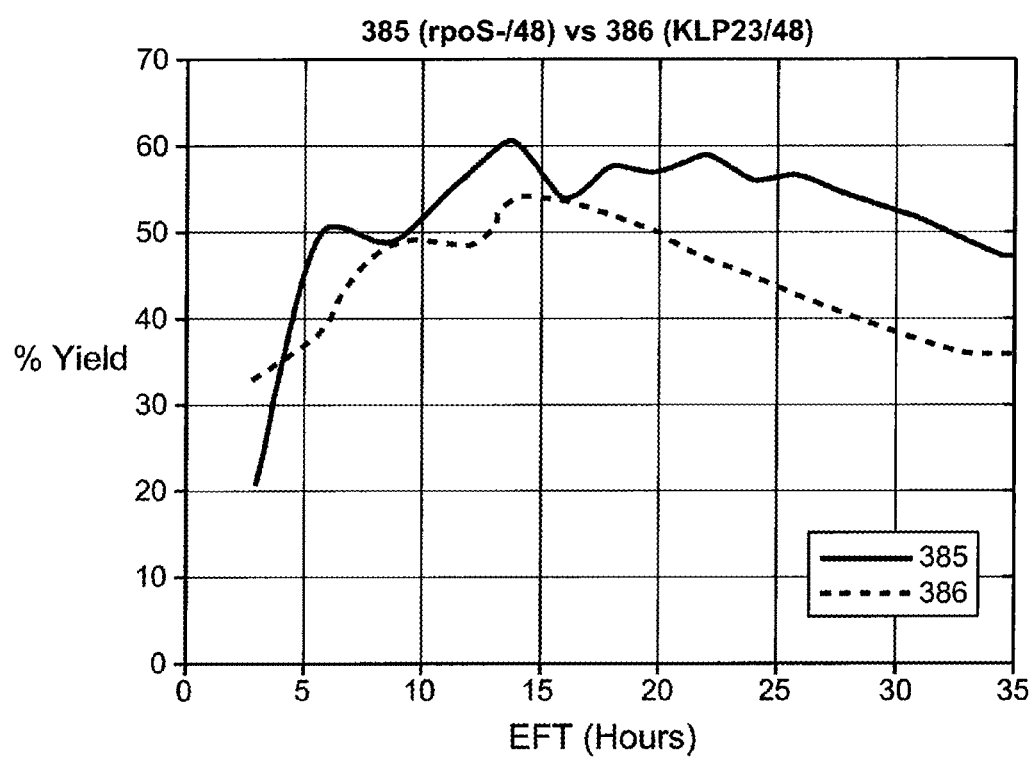

FIG. 5 illustrates the activity in an E. coli strain comprising a deletion in a rpoS gene 385(rpoS−/48) compared to a wild-type E. coli strain 386(KLP23/48) in fermentation media over time as more fully described in example 2.

FIG. 6 illustrates the nucleotide sequence of plasmid pSYCO101 (SEQ ID NO. 21).

Figure 7:
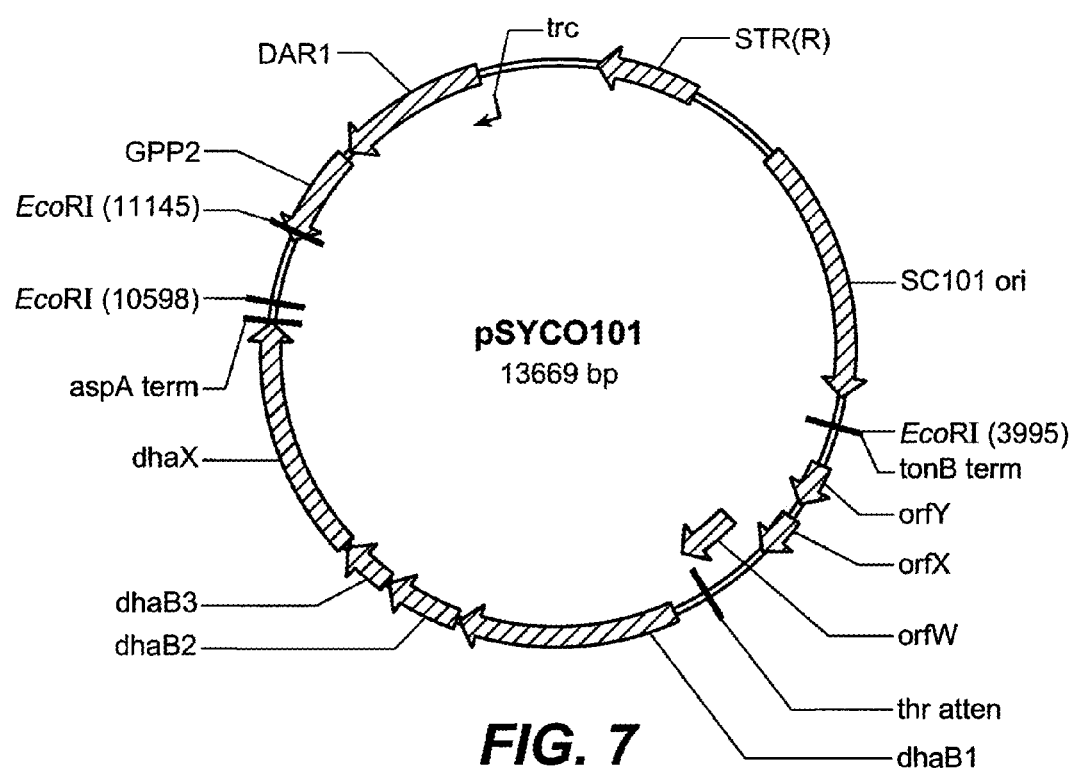

FIG. 7 illustrates a plasmid map of pSYCO 101, wherein DAR1 (dihydroxyacetone phosphate reductase) and GPP2 (glycerol-phosphate phosphatase) are glycerol pathway genes; STR(R) is a spectinomycin resistance encoding gene; pSC101 ori is an origin of replication of the plasmid; AspA term is an asparate ammonia lyase gene terminator; dhaB1-3, dhaX and orf W, X, Y are 1,3-propanediol pathway genes; Thr atten is an E. coli threonine operon attenuator; TonB term is an E. coli tonB gene terminator; and trc is the trc promoter.

DETAILED DESCRIPTION OF THE INVENTION

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, MOLECULAR CLONING: A LABORATORY MANUAL, second edition (Sambrook et al., 1989) Cold Spring Harbor Laboratory Press; CURRENT PROTOCOLS IN MOLECULAR BIOLOGY (F. M. Ausubel et al., eds., 1987 and annual updates); OLIGONUCLEOTIDE SYNTHESIS (M. J. Gait, ed., 1984); PCR: THE POLYMERASE CHAIN REACTION, (Mullis et al., eds., 1994); MANUAL OF INDUSTRIAL MICROBIOLOGY AND BIOTECHNOLOGY, Second Edition (A. L. Demain, et al., eds. 1999); MANUAL OF METHODS FOR GENERAL BACTERIOLOGY (Phillipp Gerhardt, R. G. E. Murray, Ralph N. Costilow, Eugene W. Nester, Willis A. Wood, Noel R. Krieg and G. Briggs Phillips, eds), pp. 210-213 American Society for Microbiology, Washington, D.C. and BIOTECHNOLOGY: A TEXTBOOK OF INDUSTRIAL MICROBIOLOGY, (Thomas D. Brock) Second Edition (1989) Sinauer Associates, Inc., Sunderland, Mass.

A. Definitions

Unless defined otherwise herein, all technical terms and scientific terms used herein have the same meaning as commonly understood by one of ordinary skill in the art to which this invention pertains. Singleton, et al., DICTIONARY OF MICROBIOLOGY AND MOLECULAR BIOLOGY, 2D ED., John Wiley and Sons, New York (1994) and Hale and Marham, THE HARPER DICTIONARY OF BIOLOGY, Harper Perennial, New York (1991) provide one of skill with general dictionaries of many of the terms used in this invention. Numeric ranges are inclusive of the numbers defining the range.

Unless otherwise indicated nucleic acids are written left to right in the 5' to 3' orientation and amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The references, issued patents and pending patent applications cited herein are incorporated by reference into this disclosure.

The term "global regulator" refers to a regulatory protein or RNA sequence that controls at least two operons, wherein each operon contains genes involved in different physiological roles or metabolic pathways.

The term "operon" refers to a group of genes which are transcribed as a single transcriptional unit and are subject to coordinated regulation by a common regulatory sequence.

By a "gene" is meant a segment of DNA involved in the encoding for regulatory RNA's, transfer RNA's, ribosomal RNA's, promoter regions operably linked to the expression of a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code.

As used herein a "regulatory sequence" is a nucleic acid sequence operably linked to a coding sequence to effect expression of the coding sequence. The regulatory sequence can inhibit, repress or promote the expression of the operably linked coding sequence or translation of the mRNA. Preferably, the regulatory sequence has a positive activity. i.e. binding of an endogenous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene. Regulatory sequences include promoters, enhancers, silencers, operators and transcription factors.

A "promoter" is a regulatory sequence that is involved in binding RNA polymerase to initiate transcription of a gene. A promoter will comprise two consensus sequences corresponding to a −35 homology box and a −10 homology box with a linker sequence located between the −35 box and −10 box. In one embodiment the −35 homology box corresponds to TTGACA and the −10 homology box corresponds to TATAAT. Promoters are often located upstream (5') to the transcription initiation site of an operably linked gene. A promoter may also include or be adjacent to a regulatory sequence known in the art as a silencer. A silencer sequence generally has a negative regulatory effect on expression of the gene.

An "exogenous promoter" as used herein refers to non-native promoters, synthetic promoters, and modified naturally occurring promoters. Modified naturally occurring promoters are promoters that have been derived from endogenous promoters of a host cell, wherein the endogenous promoter or a derivative thereof is reintroduced into the host cell.

Enhancers are nucleic acid regulatory sequences that can increase the utilization of promoters, and can function in either orientation (5'-3' or 3'-5') and in any location (upstream or downstream) relative to the promoter.

The term "operably linked" refers to a juxtaposition wherein the elements are in an arrangement allowing them to be functionally related. For example, a promoter is operably linked to a structural sequence if it functions as a specific binding site for RNA polymerase. Additionally a promoter is operably linked to a coding sequence if it controls the transcription of the sequence and a ribosome binding site is operably linked to a coding sequence if it is positioned so as to permit translation of the mRNA.

A "structural sequence" refers to a putative polynucleotide sequence of DNA that encodes a protein. Messenger RNA is its primary product.

The terms "arcA gene" and "arcA" used interchangeability herein refer to a polynucleotide which encodes the structural gene of ArcA or a homologue, fragment, derivative or complement thereof and having the arcA gene's function.

The terms "rpoS gene" and "rpoS" used interchangeability herein refer to a polynucleotide which encodes or comprises the rpoS RNA or a homologue, fragment, derivative or complement thereof and having the rpoS gene's function.

The terms "edd gene" and "edd" used interchangeability herein refer to a polynucleotide which encodes or comprises the edd RNA or a homologue, fragment, derivative or complement thereof and having the edd gene's function.

The terms "pta gene" and "pta" used interchangeable herein refer to a polynucleotide which encodes or comprises the pta RNA or a homologue, fragment, derivative or complement thereof and having the pta gene's function.

The terms "ackA gene" and "ackA" used interchangeably herein refer to a polynucleotide which encodes or comprises the ackA RNA or a homologue, fragment, derivative or complement thereof and having the ackA gene's function.

The terms "mgsA gene" and "msgA" used interchangeably herein refer to a polynucleotide which encodes or comprises the msgA RNA or a homologue, fragment, derivative or complement thereof and having the msgA gene's function.

The terms "ArcA" and "polypeptide having ArcA activity" refer to an aerobic respiration control protein which is a global regulatory protein encoded by the $E.$ $coli$ arcA gene or a polypeptide having substantial homology thereto and having arcA regulatory activity.

The terms "RpoS" and "polypeptide having Rpos activity" refer to a polypeptide encoded by the $E.$ $coli$ rpoS gene or a polypeptide having substantial homology thereto and having rpoS regulatory activity.

The terms "Edd" or "polypeptide having phosphogluconate dehydratase activity" refer to a polypeptide encoded by the $E.$ $coli$ edd gene or a polypeptide having substantial homology thereto and having phosphogluconate dehydratase activity. Typical of Edd is EC 4.2.1.12.

A "polypeptide having phosphogluconate dehydratase activity" refers to polypeptide which catalyzes the conversion of gluconate-6-phosphate to a) pyruvate and b) glyceraldehyde-3-phosphate in the catabolism of gluconate.

The terms "Pta" and "polypeptide having phosphotransacetylase activity" refers to a polypeptide encoded by the $E.$ $coli$ pta gene or a polypeptide having substantial homology thereto and having phosphotransacetylase activity. Typical of Pta is E.C. 2.3.1.8.

A "polypeptide having phosphotransacetylase activity" refers to a polypeptide which is capable of converting acetyl coenzyme A to acetate-phosphate.

The terms "Ack" and "polypeptide having acetate kinase activity" refer to a polypeptide encoded by the $E.$ $coli$ ackA gene or a polypeptide having substantial homology thereto and having acetate kinase activity. Typical of Ack is E.C. 2.7.2.1.

A "polypeptide having acetate kinase activity" refers to a polypeptide capable of converting acetyl phosphate to acetate or the reverse.

The terms "MgsA" and "polypeptide having methylgloxyal synthase" refer to a polypeptide encoded by the $E.$ $coli$ mgsA gene or a polypeptide having substantial homology thereto and having methylgloxyal synthase activity. Typical of MgsA is EC 4.2.3.3.

A "polypeptide having methylgloxyal synthase activity" refers to a polypeptide capable of converting dihydroxyacetone phosphate into methylglyoxal and inorganic phosphate.

The terms "phosphoenolpyruvate (PEP) carboxylase" and "Ppc" refer to a protein that catalyzes the conversion of PEP to $H_2O+CO_2$ to phosphate+oxaloacetate acid (OAA). Typical of Ppc is EC 4.1.1.31.

The term "endogenous" when referring to a gene or regulatory sequence, means that the gene or regulatory sequence originates from within the organism.

The term "exogenous" when referring to a gene or regulatory sequence, means that the gene or regulatory sequence originates from outside the organism, e.g., from another strain, species, and or genera.

The term "homologous" when referring to a gene or polynucleotide sequence, means a sequence having functional equivalence to the sequence being referred to, The homologous sequence regulates the same encoded sequence or regulates a sequence that encodes a polypeptide having the same enzymatic activity as the reference sequence even though it may not have 100% amino acid identity.

The terms "non-functional", "inactivated" and "inactivation" when referring to an operon, gene, a global regulatory sequence or a protein means that the known normal function or activity of the operon, gene, global regulatory sequence or protein has been eliminated or highly diminished. Inactivation which renders the operon, gene, global regulatory sequence or protein non-functional includes any means such as but not limited to deletions, mutations, substitutions, interruptions or insertions.

Deletions of an operon, gene or global regulator sequence may include deletion of the entire sequence of one or more genes, deletion of part of the sequence of one or more genes, deletion of the regulatory region, deletion of the translational signals and deletion of the coding sequence including flanking regions of one or more genes.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components.

A nucleic acid is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences.

As is known in the art, a DNA can be transcribed by an RNA polymerase to produce RNA, but an RNA can be reverse transcribed by reverse transcriptase to produce a DNA. Thus a DNA can encode a RNA and vice versa.

As used herein, the term "vector" refers to a polynucleotide construct designed to introduce nucleic acids into one or more cell types. Vectors include cloning vectors, expression vectors, shuttle vectors, plasmids, cassettes and the like.

DNA construct refers to a nucleic acid sequence or polynucleotide generated recombinantly or synthetically for example by in vitro PCR or other suitable techniques. the DNA construct is used to introduce nucleic acid into a host cell. The DNA construct can be incorporated into a plasmid, chromosome or nucleic acid fragment. The term DNA construct may be used interchangeably with DNA cassette, expression cassette and other grammatical equivalents.

An enzyme is "overexpressed" in a host cell if the enzyme is expressed in the cell at a higher level that the level at which it is expressed in a corresponding wild-type cell.

As used herein the term "gene" means a DNA segment that is involved in producing a polypeptide and includes regions preceding and following the coding regions as well as intervening sequences (introns) between individual coding segments (exons).

"Under transcriptional control" or "transcriptionally controlled" are terms well understood in the art that indicate that transcription of a polynucleotide sequence, usually a DNA sequence, depends on its being operably linked to an element which contributes to the initiation of, or promotes, transcription.

"Under translational control" is a term well understood in the art that indicates a regulatory process that occurs after the messenger RNA has been formed.

As used herein when describing proteins, and genes that encode them, the term for the gene is not capitalized and is italics, i.e. ppc. The term for the protein is generally not italicized and the first letter is capitalized, i.e. Ppc.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

Encompassed by the respective peptides are variants thereof in which there have been trivial substitutions, deletions, insertions or other modifications of the native peptide polypeptide which substantially retain the respective peptide activity characteristics, particularly silent or conservative substitutions. Silent nucleotide substitutions are changes of one or more nucleotides which do not change any amino acid of the respective peptide. Conservative substitutions include substitutions within the following groups: glycine, alanine; valine, isoleucine, leucine; aspartic acid, glutamic acid; asparagine, glutamine; serine, threonine; lysine, arginine; and phenylalanine, tyrosine. Such conservative substitutions are not expected to interfere with the respective biochemical activity, particularly when they occur in structural regions (e.g., alpha helices or beta pleated sheets) of the polypeptide, which can be predicted by standard computer analysis of the amino acid sequence of *E. coli* peptide.

The terms "PTS", "PTS system" and "Phosphoenolpyruvate (PEP)-dependent phosphotransferase transport system" (E.C. 2.7.1.69) refer to the PEP dependent sugar uptake system which transports and phosphorylates glucose into a cell.

The terms "phenotypically PTS$^-$/Glu$^-$", "PTS$^-$/Glu$^-$ phenotype" and PTS$^-$/Glu$^-$ refer to a cell which has a significantly reduced ability to utilize glucose as a carbon source because the PTS, normally utilized by such strains to transport and phosphorylate glucose is inactivated.

The terms "phenotypically PTS$^-$/Glu$^+$", "PTS$^-$/Glu$^+$ phenotype" and PTS$^-$/Glu$^+$ refer to a cell that is capable of utilizing glucose as a carbon source despite the inactivation of PTS. A PTS$^-$/Glu$^+$ strain will have a specific growth rate of at least 0.4 per hour (0.4 hr$^{-1}$).

The term "specific growth rate ($\mu$)" refers to the increase of mass or cell number per time. In one embodiment the specific growth rate will be at least 0.4 hr$^{-1}$, at least 0.5 hr$^{-1}$, at least 0.6 hr$^{-1}$, at least 0.7 hr$^{-1}$ and at least 0.8 hr$^{-1}$ or greater.

The phrase "enhanced production" refers to an increase in the amount of desired end-product produced by a genetically engineered (altered) microorganism according to the invention as compared to the production of the same end-product in a corresponding wild-type (unaltered) microorganism. Enhanced production may be determined as an increased amount of end product produced per unit of carbon substrate or per amount of microorganism.

By "enhanced growth rate" is meant an increased growth rate of the altered bacterial host according to the invention as compared to the growth rate of the corresponding unaltered bacterial host.

By "aerobic conditions" is meant that there is sufficient $O_2$ available in the fermentation medium that the repressive regulation by arcA in an unaltered bacterial host cell is initiated. In one embodiment, $O_2$ flow levels of greater than about 0.5 liters per minute, greater than about 1.0 liters per minute, greater than about 2.0 liters per minute, greater than about 3.0 liters per minute, greater than about 4.0 liters per minute, and greater than about 5.0 liters per minute per 14 liter tank are contemplated. In another embodiment, not more than 15 liters/min per 14 liter tank is contemplated. Also between about 0.5 to 15 liters per minute and between about 0.5 to 12 liters per minute of oxygen flow per 14 liter tank are contemplated.

By "biomass" is meant, when referring to a host cell, the weight of the host cells in the fermentation media.

The term "culturing" means the fermentative bioconversion of a carbon substrate to a desired end product within a reaction vessel. Typical reaction vessels include but are not limited to vats, bottles, flasks, bags, bioreactors and any other suitable receptacle.

Bioconversion refers to the contacting a microorganism with a carbon substrate to convert the carbon substrate to a desired end product.

As used herein, the term "carbon source" encompasses suitable carbon substrates ordinarily used by microorganisms, such as 6 carbon sugars, including but not limited to glucose (G), gulose, lactose, sorbose, fructose, idose, galactose and mannose all in either D or L form, or a combination of 6 carbon sugars, such as glucose and fructose, and/or 6 carbon sugar acids.

The terms "isolating" and "isolation" mean to separate a compound from other materials. Isolation is meant to achieve a purity of at least 70%, 75%, 80%, 85%, 90%, 95%, 97% and 99%.

The term "isolate" with reference to a nucleic acid or polypeptide means the nucleic acid or polypeptide is removed from at least one component with which it is naturally associated.

The term "introduced" in the context of inserting a nucleic acid sequence into a cell, means protoplast fusion, transfection, transformation, transduction, conjugation and the like.

The term "transformed" means the cell has a non-native (heterologous) polynucleotide sequence integrated into is genome.

The term "chromosomal integration" refers to a process where a polynucleotide is introduced into the chromosome of a cell As used herein, the term "bacteria" refers to any group of microscopic organisms that are prokaryotic, i.e., that lack a membrane-bound nucleus and organelles. All bacteria are surrounded by a lipid membrane that regulates the flow of materials in and out of the cell. A rigid cell wall completely surrounds the bacterium and lies outside the membrane.

A "genetically engineered microorganism" refers to a microorganism having a modified genetic sequence as compared to the original/initial derivative and/or wild type.

An "altered bacterial host" according to the invention is a genetically engineered bacterial host cell having an inactivated endogenous arcA or rpoS and an overexpressed ppc. In one embodiment, an altered bacterial host will have an enhanced level of production of a desired compound compared to the level of production of the same desired compound in a corresponding unaltered bacterial host grown under essentially the same growth conditions.

An "unaltered bacterial host cell" according to the invention is a bacterial host cell wherein the endogenous arcA or endogenous rpoS gene is not inactivated and remains functional.

As used herein "chromosomal integration" is a process whereby an introduced polynucleotide is incorporated into a host cell chromosome. The process preferably takes place by homologous recombination.

As used herein, "modifying" the level of protein or enzyme activity produced by a host cell refers to controlling the levels of protein or enzymatic activity produced during culturing, such that the levels are increased or decreased as desired.

As used herein, the term "modified" when referring to nucleic acid or a polynucleotide means that the nucleic acid has been altered in some way as compared to a wild type nucleic acid, such as by mutation in; substitution, insertion, deletion of part or all of the nucleic acid; or by being operably linked to a transcriptional control region. Examples of mutations include but are not limited to point mutations, frame shift mutations and deletions of part or all of a arcA gene or rpoS gene.

"Desired product" as used herein refers to the desired compound to which a carbon substrate is bioconverted into. Exemplary desired products are pyruvate, chorismate, PEP, glycerol, OAA, and succinate.

By "metabolic product" is meant any sugar, amino acid, protein, alcohol, acid, organic compound, non-organic compound, or derivative or chemically modified version of any of the above which is produced as a result of a biosynthetic pathway.

As used herein, the term "recombinant" refers to a host cell that has a modification of its genome, e.g., as by the addition of nucleic acid not naturally occurring in the organism or by a modification of nucleic acid naturally occurring in the host cell.

A polynucleotide or polypeptide having substantial homology to another polynucleotide or polypeptide will have a certain percentage (for example, 80%, 85%, 90%, 95%, 96%, 97% or 99%) of "sequence identity" to another sequence, and means that, when aligned, that percentage of bases or amino acids are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2. Another sequence software program that could be used is the TFastA Data Searching Program available in the Sequence Analysis Software Package Version 6.0 (Genetic Computer Group, University of Wisconsin, Madison, Wis.). One skilled in the art will recognize that sequences encompasses by the invention are also defined by the ability to hybridize under stringent or moderate conditions with the described sequences.

A nucleic acid is "hybridizable" to another nucleic acid when a single stranded form of the nucleic acid can anneal to the other nucleic acid under appropriate conditions of temperature and solution ionic strength. Hybridization and washing conditions are well known and exemplified in Sambrook (1989) supra, (see in particular chapters 9 and 11). Low stringency hybridization conditions correspond to a Tm of 55° C. (for example 5×SSC, 0.1% SDS, 0.25 milk and no formamide or 5×SSC, 0.5% SDS and 30% formamide). Moderate stringency hybridization conditions correspond for example, to 6×SSC, 0.1% SDS, 0.05% milk with or without formamide, and stringent hybridization conditions correspond for example, to a Tm of 65° C. and 0.1×SSC and 0.1% SDS.

As used herein, the term "comprising" and its cognates are used in their inclusive sense; that is, equivalent to the term "including" and its corresponding cognates.

"A," "an" and "the" include plural references unless the context clearly dictates otherwise.

"NCBI" refers to the National Center for Biotechnology Information, Natl Library Med. (www.ncbi.nlm.nih.gov/).

"ATCC" refers to the American Type Culture Collection international depository located at 10801 University Blvd. Manassas, Va. 201110.

B. Preferred Embodiments

It would be highly advantageous to metabolically engineer bacteria to regulate the flow of compounds through various biochemical pathways resulting in an increase in the production of desired compounds, an increase in growth rate of engineered cells or an increase in biomass production of the engineered cells.

The present invention encompasses the inactivation of an arcA gene and the RNA encoded thereby and/or the inactivation of a rpoS gene, said inactivation inhibiting the ability of the gene to down regulate expression of metabolic products.

1. Host Cells—

Preferred host cells that may be genetically engineered according to the invention are bacterial cells. In particular bacterial cells of *Salmonella, Citrobacter, Pseudomonas, Ralstonia*, strains within the family of Enterobacteriaceae and eubacteria.

The family "Enterobacteriaceae" refers to bacterial strains having the general characteristics of being gram negative and being facultatively anaerobic. Included in the family of Enterobacteriaceae are *Erwinia, Enterobacter, Gluconobacter, Serratia, Klebsiella, Escherichia* and *Pantoea*. In the present invention, particularly preferred Enterobacteriaceae are *Erwinia, Klebsiella, Escherichia* and *Pantoea*, and most preferred are fermentation strains of *Escherichia* and *Pantoea*. Reference is also made to Kageyama et al., (1992) *International J. Sys. Bacteriol.* 42:203. In one embodiment, the preferred host cell is a *Pantoea* cell. *Pantoea* includes *P. agglomerans, P. dispersa, P. punctata, P. citrea, P. terrea, P. ananas* and *P. stewartii* and in particular, *Pantoea citrea*. *Pantoea citrea* is a preferred *Pantoea* strain, for example ATCC No. 39140. *Pantoea citrea* has sometimes been referred to as *Erwinia citreus* or *Acetobacter cerinus*. Thus, it is intended that the genus *Pantoea* include species that have been reclassified, including but not limited to *Erwinia citreus* or *Acetobacter cerinus*. In another preferred embodiment, the host strain is an *E. coli* cell, for example KLP23 as disclosed in WO 01/012833A2; RJ8N having ATCC No. PTA 4216 and MG1655 having ATCC No. 700926.

In another embodiment the host strain is one that is capable of using a PTS for carbohydrate transport. A general review of the PTS can be found in (Postma et al., 1993, *Microbiol. Rev.* 57:543-594; Romano et al., 1979, *J. Bacteriol.* 139:93-97 and Saier et al. 1990, In: BACTERIAL ENERGETICS pp. 273-299, T. A. Krulwich, Ed. Academic Press, NY). Also reference is made to Meadow et al. (1990) *Annu. Rev. Biochem.* 59:497-542

In one preferred embodiment the host strain encompassed by the invention is a strain that was originally capable of utilizing a PTS for carbohydrate transport but has been altered to have an inactive PTS (phenotypically PTS$^-$/Glu$^-$).

Selection of PTS$^-$ cells can be achieved using techniques available to those skilled in the art. Inactivation will effectively reduce PEP phosphorylation to undetectable levels as measured by PEP-dependent phosphorylation of 2-deoxy-D-glucose using the protocols described by Gachelin, G. (1969). *Biochem. Biophys. Acta.* 34:382-387; Romero, et al., (1979) *J. Bact.* 139:93-97; or Bouvet and Grimont., (1987) *Ann. Inst. Pasteur/Microbiol.* 138:3-13. Also PEP phosphorylation assays are useful in determining the level of PTS$^-$ expression.

PST$^-$/Glu$^-$ host cells may be selected from PTS wild-type host cells by inactivation of at least one gene encoding part or all of the enzymes comprising the PTS. By way of example, in one embodiment, the PTS is inactivated by the deletion of at least one gene selected from the group consisting of ptsI, ptsH and crr encoding the EI, HPr and IIA$^{Glc}$ proteins of the PTS respectively (Postma, et al (1993) *Microbiol. Rev.* 57:543-594). In other embodiments, at least two of the genes are inactivated. The nucleotide sequences of ptsI, ptsH and crr have been determined (Saffen et al., (1987) *J. Biol. Chem.* 262:16241-16253; Fox et al., (1984) *Biochem. Soc. Trans.* 12:155-157; Weigel et al., (1982) *J. Biol. Chem.* 257:14461-14469 and DeReuse et al., (1988) *J. Bacteriol.* 176:3827-3837). In other embodiments, the inactivation of all three genes ptsI, ptsH and crr by deletion will effectively reduced PEP phosphorylation to undetectable levels.

A nonlimiting example of a method employed to inactivate the PTS is as follows. It is known that in *E. coli* the ptsI, ptsH and crr are linked together in an operon. The ptsHIcrr operon in *E. coli* strains such as JM101 (Yanisch-Perron et al. (1985) *Gene* 33:103-119) and strain PB103 (Mascarenhas (1987) PCT WO/87/01130) can be inactivated by deletion using a generalized transduction method as described by Silhavy, et al. (1984) In: EXPERIMENTS WITH GENE FUSIONS, pp 110-112, Cold Spring Harbor Laboratory Press, NY. P1vir phage is used to perform the transduction and strain TP2811 (Levy et al., (1990) *Gene* 86:27-33) can be used as the donor of the ptsHIcrr deletion. The process can be carried out in two stages. First, a cell-free suspension of phage is prepared by growing bacteriophage P1vir on strain TP2811. In the TP2811 strain most of the ptsHIcrr operon has been deleted and a kanamycin-resistant marker may be inserted in the same DNA region (Levy et al., (1990) *Gene* 86:27-33). The obtained P1vir lysate was able to transduce the ptsHIcrr deletion and kanamycin resistance marker simultaneously. Secondly, these phage can be used to infect the recipient strains, JM101 or PB103 and transductants may be selected by plating the infected cells on MacConkey-glucose plates containing kanamycin. The recipient strains (JM101 and PB103) are kanamycin sensitive and form red colonies on MacConkey-glucose plates. The MacConkey-glucose plates contain an indicator dye that, depending on the pH, can vary from white to deep red. If the cells can transport glucose at a fast rate, normally they will secrete organic acids and produce red colonies. If glucose transport is diminished or absent, the cells will not produce organic acids and the colonies will be white. This enables one to ascertain whether the host cell exhibits a glucose$^+$ (PTS$^-$/Glu$^+$) or glucose$^-$ (PTS$^-$/Glu$^-$) phenotype.

To corroborate if transductants have a PTS$^-$/Glu$^-$ phenotype they can be selected and inoculated in minimal medium containing glucose as the only carbon source. One would expect after incubation (for 12 hours at 37° C.) the transductants would have no detectable cell growth and the PTS parent strains would grow very well (WO 96/34961). Based on the above results of WO 96/34961 the PTS$^-$ derivative of JM101 was designated PB11 and the PTS$^-$ derivative of PB103 was designated NF6.

Another test for the absence of the PTS system is based on the fact that PTS⁻ strains become resistant to the antibiotic fosfomycin Cordaro et al., (1976) *J. Bacteriol* 128:785-793.

One further nonlimiting method which may be used to inactivate PTS in a bacterial host includes inserting or modifying a repressor binding region operably linked with a gene encoding an expressed protein such that the expression of the gene occurs in the presence of a specific molecule. For example, the lac operator is a DNA sequence recognized by the Lac repressor. If this operator is located in the proper position, relative to the promoter, then if the repressor is bound to the operator, it will interfere with the binding of the RNA polymerase and block gene transcription. This blockage can be removed by the addition of the inducer IPTG (isopropyl-β-D-thiogalactoside). The level of repression and/or induction will depend on the strength of the promoter, the location and sequence of the operator, as well as the amount of the repressor and the inducer (Muller J. et al., (1996) *J. Mol. Biol.* 257:21-29). The lac operator is used to regulate a number of promoters, among them several variants of the lac promoter and the hybrid trc promoter.

Another nonlimiting method to affect a PTS⁻/Glu⁻ phenotype includes the incorporation of a promoter which affects the expression of the structural gene sequence when certain conditions are present. For example, the Pm promoter from the TOL plasmid can be used to control gene expression. In this system, gene expression is achieved when benzoate or toluate is added to the media. (Mermod et al., (1986) *J. Bact.* 167:447-454). Still a further nonlimiting method to affect a PTS⁻ phenotype is to alter the mRNA stability as described by Carrier and Keasling (1997) *Biotechnol. Prog.* 13:699-708.

To increase or redirect carbon flow to desired metabolic pathways in inactivated PTS host cells, glucose transport and phosphorylation must be deregulated or amplified. Therefore in one preferred embodiment a preferred host cell will have a restored glucose+ (PTS⁻/Glu⁺) phenotype; that is a PTS⁻/Glu⁻ host cell is modified to restore the glucose⁺ phenotype, thereby obtaining a PTS⁻/Glu⁺ phenotype. WO 96/34961 and Hernandez-Montalvo et al. (2001) *Appl Microbiol. Biotechnol* 57:186-191 described *E. coli* strains having a PTS⁻/Glu+ phenotype.

2. Inactivation of Global Regulatory Genes.
a. Genes to be Inactivated:

To achieve beneficial increased production levels of desired products, an increased growth rate or an increased biomass of a host cell, the inventors developed a method for identifying beneficial modifications comprising the step of selecting global regulators that have a regulatory effect on a multitude of genes that express polypeptides having beneficial enzymatic activities and modifying the global regulatory genes. Exemplary global regulators include, but are not limited to arcA, rpoS, Fnr (NP 415850), OxyR (NP 418396), CRP (NP 417816), Fur (NP 414622) and H-NS (P08936).

In a preferred embodiment the modified global regulatory gene is an arcA gene and homologous genes coding for RNAs or proteins having essentially the same function and having at least 70%, 75%, 80%, 85%, 90%, 93%, 96%, 97% and 99% sequence identity thereto. The arcA gene has been characterized (NCBI AE000510). It has also been identified and characterized in *Samonella typhimurium* LT2 (NC 003197), *Samonella enterica* (NC 003098) and *Stretomyces coelicolor* (NC 003888). The ArcA sequence from *E. coli* has been deposited in the NCBI database with the number NP 418818. (Also reference is made to GenBank Accession No. U00096). The ArcB sequence from *E. coli* has been deposited in the NCBI database with the number NP 417677. (Iuchi et al., (1990) *Mol. Microbiol* 4:715-727). Therefore in one embodiment a polypeptide having ArcA activity will have at least 70%, at least 80%, at least 85%, at least 90%, at least 95% and at least 98% sequence homology to the *E. coli* ArcA having the sequence of NP 418818. The arcA/arcB regulatory system regulates more than one operon which is involved in respiratory and fermentative metabolism in response to oxygen deficiency. The reference Lynch et al., ((1996) REGULATION OF GENE EXPRESSION IN ESCHERICHIA COLI. Eds. Lin et al., Chapman and Hall NY) list numerous genes that may be regulated by the ArcA/ArcB system. Some of these genes include aceB, acn, arcA, cob, cyd (A and B), cyo (A, B, C, D and E), fadb, fdn(G, H and I), focA, pfl, fumA, glpD, gitA, hemA, hya(A-F), icd, ict(P, R and D), mdh, nuo(A-N), pdh, ace(E and F), lpd, pdu, pocR, sdh (A-D), soda, suc(A-D) and traY; and particularly, aceB, arcA, cyd (A and B), cyo (A, B, C, D and E), gltA, mdh, nuo(A-N), sdh (A-D) and suc(A-D).

In another preferred embodiment the modified global regulatory gene is rpoS and homologous genes coding for RNAs or protein having essentially the same function and having at least 70%, 75%, 80%, 85%, 90%, 93%, 96%, 97% and 99% sequence identity thereto. The rpoS gene has been characterized and the rpoS sequence from *E. coli* has been deposited in the NCBI database with the number NP 417221. Therefore in one embodiment a polypeptide having RpoS activity will have at least 70%, at least 80%, at least 85%, at least 90%, at least 95% and at least 98% sequence homology to the *E. coli* RpoS having the sequence of NP 417221. The RNA polymerase sigma factor which is the product of the rpoS gene binds to the core RNA polymerase under a variety of stress factors. While the number and types of genes controlled regulated by rpoS will vary, the reference of Hengge-Aronis ((1996) in ESCHERICHIA COLI AND SALMONELLA: CELLULAR AND MOLECULAR BIOLOGY, Eds. Neidhardt et al., ASM Press, Washington D.C. pages 1492-1512) list numerous genes that may be regulated by rpoS. Some of these genes include aidb, aldb, app(A, B, C, y), bolA, cbdAB, cbpA, cfa, csg(A, B, D, E, F and G), cs/E, dacc, dps, emr(A and B), fic, fts(A, Q and Z), ga/(E, K and T), g/g(A and S), glpD, gor, hde(A and B), him(A and D), htrE, hya(A, B, C, D, E and F), kat(E and G), lacZ, ldcC, mcc, osm(B and Y), ots(A and B), poxB, pro(P, V, W, and X), topA, treA, wrbA, and xthA; and particularly, aldb, dps and poxB.

The genes of homologs of *E. coli* arcA and rpoS in other species or strains can be obtained by generating cDNA from RNA from such species using any technique known in the art, such as using Riboclone cDNA Synthesis Systems AMV RT (Promega, Madison, Wis.), then probing such cDNA with radiolabeled primers containing various portions (e.g. 30 or 40 bases long) of the sequences of the *E. coli* arcA or rpoS disclosed herein and in references cited herein. To obtain homologs of arcA and rpoS degenerate primers can encode the amino acid sequence of the disclosed *E. coli* polypeptides but differ in codon usage from the sequences disclosed. Additional known hybridization techniques and computer-automated sequence comparisons and identification using algorithms such as BLAST may be used to identify homologous sequences.

At least one host cell chromosomal region can be modified by inactivation of the region coding for the expression of a global regulator arcA or the global regulator rpoS and those homologous thereto. Inactivation may occur through the deletion, insertion or substitution of at least one nucleotide in the genomic coding region of the wild type host cell. In a preferred embodiment, inactivation of one or more genes will preferably be a stable and non-reverting inactivation. In a further embodiment, inactivation results from deletion of part or all of the arcA or rpoS gene and those homologous thereto.

The deletion may be partial as long as the sequences left in the chromosome are too short for biological activity of the gene. In some embodiments an altered bacterial cell will include more than one inactivated gene, for examples at least two inactivated genes, at least three inactivated genes, at least four inactivated genes, at least five inactivated genes, at least six inactivated genes or more. The inactivated genes may be contiguous to one another or may be located in separate regions of the host cell chromosome. The inactivated gene may have a necessary function under certain conditions but the gene is not necessary for host cell strain viability under laboratory conditions such as growth in a fermentation, in a shake flask, in plate media and the like.

b. Construction of DNA Integration Cassettes for Gene Inactivation

Typically DNA integration cassettes (also referred to as DNA mutagenic cassettes or constructs) which are useful for modifying endogenous chromosomal arcA, rpoS and homologous regulatory regions thereto include homologous nucleic acid sequences of the regulatory region encoding the expression of the global regulators to be inactivated, a selectable marker, and sequences for allowing autonomous replication or chromosomal integration, such as recombinase recognition sites.

The nucleic acid sequences homologous to upstream (5') regions of a gene encoding a global regulatory protein. These homologous sequences will preferably flank a first recombinase recognition site (5' thereto) and a second recombinase site (3' thereto). Nucleic acid sequences homologous to upstream (5') regions of a gene encoding a global regulatory protein include sequences derived from a) a sequence 5' to the endogenous regulatory region that is targeted for modification, and b) a sequence 3' of the endogenous regulatory region that is targeted for modification. The 3' sequence may include parts of a global regulatory protein coding sequence. A homologous flanking sequence may include from about 2 to 500 bp, about 5 to 250 bp, about 5 to 200 bp, about 5 to 100 bp and about 5 to 50 bp.

A mutagenic DNA cassette encompassed by the invention will include a selectable marker and a number of genes can be used to detect insertion of the gene in *E. coli*. Some of these genes confer selectable phenotypes. In this case, media conditions can be established so that only colonies which have expression of these genes activated will grow. Other genes confer phenotypes which can be screened. A screenable phenotype can often yield information about levels of gene expression. While any desired marker can be used, based on these properties, useful antibiotic resistance (AnbR) markers include but are not limited to, $Cm^R$, $Km^R$ and $Gm^R$. A preferred non-limiting example of a selectable marker is a chloramphenicol acetyltransferase (CAT) gene. In a preferred embodiment, the selectable marker will be flanked on both sides by a recombinase recognition site. It is advantageous if the selective marker is removed after integration into the target cell.

Recombinase sites are well known in the art and generally fall into two distinct families based on their mechanism of catalysis and reference is made to Huang et al., (1991) *NAR.* 19:443; Datsenko and Warner (2000) *Proc. Natl. Acad. Sci.* 97:6640-6645 and Nunes-Duby, D, et al, (1998) *NAR* 26:391-406. Preferably the recognition sites are the same. One well known recombination system is the *Saccharomyces* Flp/FRT recombination system, which comprises a Flp enzyme and two asymmetric 34 bp FRT minimum recombination sites (Zhu et al., (1995) *J. Biol. Chem.* 270:11646-11653). A FRT site comprises two 13 bp sequence inverted and imperfectly repeated, which surround an 8 bp core asymmetric sequence where crossing-over occurs. (Huffman et al., (1999) *J. Mol. Biol.* 286:1-13). Another well known recombinase system is the Cre/loxP site-specific recombination system of bacteriophage P1, which comprises a Cre enzyme and two asymmetric 34 bp loxP recombination sites (Sternberg and Hamilton (1981) *J. Mol. Biol.* 150:467-486); Palmeros, B, et al (2000) *Gene* 247:255-264; Hoess et al. (1986) *NAR* 14:2287-2300; Sauer B. (1994) *Curr. Opinions in Biotechnol.* 5:521-527). A loxP site comprises two 13 bp sequences, inverted and imperfectly repeated, which surround an 8 bp core asymmetric sequence, where crossing-over occurs. The Cre-dependent intramolecular recombination between two parallel loxP sites results is excision of any intervening DNA sequence as a circular molecule, producing two recombination products, each containing one loxP site (Kilby et al., (1993) *Trends Genet.* 9:414-421).

C. Transformation

Once a mutagenic DNA integration cassette is constructed it may be introduced into a host cell by means well known in the art. Some of these transfer techniques include transformation, transduction, conjugation and protoplast fusion. A variety of transformation procedures are known by those of skill in the art for deleting or overexpressing genes or gene fragments in the host cell chromosomes. General transformation procedures are taught in CURRENT PROTOCOLS IN MOLECULAR BIOLOGY (vol. 1, edited by Ausubel et al., John Wiley & Sons, Inc. 1987, Chapter 9) and include calcium phosphate methods, transformation using DEAE-Dextran and electroporation. Reference is also made to U.S. Pat. No. 5,032,514; Potter H. (1988) *Anal. Biochem* 174:361-373; and Sambrook, J. et al., MOLECULAR CLONING: A LABORATORY MANUAL, Cold Spring Harbor Laboratory Press (1989).

Whether a host cell has been transformed can be detected by the presence/absence of marker gene expression which can suggest whether the nucleic acid of interest is present. However, its expression should be confirmed. For example, if the nucleic acid encoding a pathway enzyme is inserted within a marker gene sequence, recombinant cells containing the insert can be identified by the absence of marker gene function.

Expression of the marker gene in response to induction or selection usually indicates expression of the enzyme as well. Alternatively, host cells which contain the coding sequence for a pathway enzyme and express the enzyme may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein. Additionally, the presence of the enzyme polynucleotide sequence in a host microorganism can be detected by DNA-DNA or DNA-RNA hybridization or amplification using probes, portions or fragments of the enzyme polynucleotide sequences.

In a preferred embodiment once the mutagenic DNA cassette is introduced into a host cell an endogenous global regulatory gene is inactivated, and preferably an arcA gene, a rpoS gene or homologous genes thereto is inactivated by deletion and preferably deleted by homologous recombination. This general methodology is described in Datsenko and Warner (2000) proc. Natl. Acad. Sci. 97:6640-6645).

Alternatively when the arcA gene is to be deleted, a chloramphenicol resistance gene may cloned into a unique restriction site found in the arcA gene. The $Cm^R$ gene may then be inserted into the structural coding region of the gene at the respective site. Modification is then transferred to the chromosome of a E. coli arcA by homologous recombination using a non-replicating R6K vector. The Cm$^R$ gene may then be removed from the arcA coding region leaving an interrupting spacer in the coding region, which results in inactivation of the coding region. In another embodiment, the Cm$^R$ gene may be inserted into the coding region in exchange for portions of the coding region. Subsequent removal of the Cm$^R$ gene without concomitant reinsertion of the exchanged out portion of the coding region results in an effective deletion of a portion of the coding region, inactivating such region. The end result is that the deleted gene is effectively non-functional.

In another embodiment, inactivation is by insertion. For example a DNA construct will comprise a nucleic acid sequence having the arcA gene interrupted by a selective marker. The selective marker will be flanked on each side by sections of the arcA gene coding sequence. The DNA construct aligns with essentially identical sequences of the endogenous arcA in the host chromosome and in a double crossover event the endogenous arcA gene is inactivated by the insertion of the selective marker.

In another embodiment, inactivation is by insertion in a single crossover event with a plasmid as the vector. For example, the arcA gene to be excised is aligned with a plasmid comprising polynucleotides of the arcA gene or part of the gene coding sequence and a selective marker. The selective marker may be located within the gene coding sequence or on a part of the plasmid separate from the gene. The vector is integrated into the host cell chromosome, and the gene is inactivated by the insertion of the vector in the coding sequence.

Inactivation may also occur by a mutation of the gene. Methods of mutating genes are well known in the art and include but are not limited to chemical mutagenesis, site-directed mutation, generation of random mutations, and gapped-duplex approaches. (U.S. Pat. No. 4,760,025; Moring et al., *Biotech.* 2:646 (1984); and Kramer et al., *Nucleic Acids Res.* 12:9441 (1984)).

Inactivation may also occur by applying the above described inactivation methods to the respective promoter regions of the desired genomic region.

D. Construction of DNA Cassettes for Overexpression of PPC

The present invention encompasses overexpressing a ppc gene. The ppc gene and homologous genes thereto can be overexpressed by the introduction of a DNA cassette comprising of multiple copies of the ppc gene or by the introduction of a DNA cassette comprising a regulatory sequence including a promoter operably linked with a ppc.

In one preferred embodiment overexpression is accomplished by replacing an endogenous regulatory region of a chromosomal ppc gene with a exogenous promoter. As used herein with respect to ppc, an exogenous promoter is a promoter other than a naturally occurring promoter, which is operably linked to an endogenous coding region of a phosphoenolpyruvate carboxylase (Ppc) in a host cell and includes but is not limited to non-native promoters, synthetic promoters, and modified naturally occurring promoters which include a) native endogenous promoters which are operably linked to a polynucleotide encoding a Ppc, wherein the native promoter has been altered and then reintroduced into the host cell chromosome and b) native endogenous promoters which are not operably linked to a polynucleotide encoding a Ppc.

In a preferred embodiment a DNA cassette is constructed which comprises regulatory sequences including an exogenous promoter as defined above and further includes a selectable marker; sequences allowing autonomous replication or chromosomal integration, such as recombinase recognition sites; and flanking sequences, which are located upstream (5') and downstream (3') of the recombinase recognition sites.

A regulatory region and specifically including a promoter useful in a DNA cassette according to the invention includes sequences of between about 20 to 200 bp, of between about 20 to 150 bp and of between about 20 to 100 bp. Exemplary exogenous promoters include glucose isomerase (GI) (NCBI NC 003074), trc, Tac, Trp, Lac, LacUV5, Bla, $P_{tac1}$, $P_R$, $P_{RM}$, $P_{A1}$, $P_{A2}$, $P_{A3}$ and $P_L$ and derivative promoters thereof (Deuschle et al., (1986) (*EMBO J.* 5: 2987-2994; (Amann et al., (1983) *Gene* 25:167-178 and Amore et al. (1989) *Appl. Microbiol. Biotechnol.* 30:351-357). Preferred promoters include the trc promoter and derivatives thereof (Amann et al., (1983) supra) and the GI promoter (also known as a xylose isomerase promoter), short GI promoters and derivatives thereof. Reference is made to Amore et al. (1989) supra. 30:351-357. The sequence of a segment of the GI promoter (+50 to −7 of the −10 box) is set forth in SEQ ID NO. 19 5' CGAGCCGTCACGCCC TTGACAATGCCACATCCTGAGCA<u>AATAAT</u> 3' wherein the −35 box is represented by TTGACA and the −10 box is represented by AATAAT. Additionally, a preferred promoter is the short 1.6GI promoter as illustrated in SEQ ID NO. 20.

A derivative promoter may include a modification to at least one nucleotide in a position corresponding to a nucleotide in the −35 box, linker region or −10 box. In a preferred embodiment these derivative promoters are altered in a position corresponding to a position in the −35 box. Particularly preferred derivative promoters include a modification to a −35 box corresponding to TTGACA and TTTACA. Some TTGACA modifications include TTGAAA, TTCAC and CTGACA. One particular modification is to the position corresponding to position −35. Particularly preferred derivative promoters also include a modification to a −10 box corresponding to TATAAT, TAAGAT and TATGTT. Linker regions may also be modified (Burr et al., (2000) *NAR* 28:1864-1870). Preferably linker regions whether modified or unmodified are between 14 to 20 bp in length, preferably 16 bp, 17 bp, 18 bp and 19 bp. Those skilled in the art are well aware of methods used to make modifications in promoters and the present invention is not limited by these methods. One exemplary method includes use of the Quikchange Kit (Stratagene); Reference is also made to WO 98/07846; Russell and Bennett (1982) *Gene* 231-243 and Sommer et al. (2000) *Microbiol.* 146:2643-2653.

A selectable marker can be used to detect insertion of the ppc gene in a host cell as previously described.

In a preferred embodiment, a DNA cassette comprising the promoter to be integrated into a host cell chromosome at a ppc target site will include a selectable marker flanked on both sides by a recombinase recognition site. Recombinase sites are described above for the DNA cassettes useful for inactivation of arcA and rpoS. Also see Huang et al., (1991) *NAR.* 19:443; Datsenko and Warner (2000) *Proc. Natl. Acad. Sci.* 97:6640-6645; Nunes-Duby, D, et al, (1998) *NAR* 26:391-406; Zhu et al., (1995) *J. Biol. Chem.* 270:11646-11653; Huffman et al., (1999) *J. Mol. Biol.* 286:1-13; Sternberg and Hamilton (1981) *J. Mol. Biol.* 150:467-486); Palmeros, B, et al (2000) *Gene* 247:255-264; Hoess et al. (1986) *NAR* 14:2287-2300; and Sauer B. (1994) *Curr. Opinions in Biotechnol.* 5:521-527).)

One preferred recombinase system is the Cre/loxP site-specific recombination system of bacteriophage P1, which comprises a Cre enzyme and two asymmetric 34 bp loxP recombination sites (Sternberg and Hamilton (1981) *J. Mol. Biol.* 150:467-486); Palmeros, B, et al (2000) *Gene* 247:255-264; Hoess et al. (1986) *NAR* 14:2287-2300; Sauer B. (1994) *Curr. Opinions in Biotechnol.* 5:521-527 and Kilby et al., (1993) *Trends Genet.* 9:414-421). Preferably the recognition sites are the same.

An integration DNA cassette useful for effecting overexpression according to the invention will also include nucleic acid sequences homologous to upstream (5') regions of a gene encoding a Ppc protein. These homologous sequences will preferably flank the first recombinase recognition site (5' thereto) and the promoter (3' thereto). Nucleic acid sequences homologous to upstream (5') regions of a gene encoding a Ppc protein include sequences derived from a) a sequence 5' to the endogenous regulatory region that is targeted for modification, and b) a sequence 3' of the endogenous regulatory region that is targeted for modification. The 3' sequence may include parts of a Ppc coding sequence. A homologous flanking sequence may include from about 2 to 250 bp, about 5 to 200 bp, about 5 to 150 bp, about 5 to 100 bp and about 5 to 50 bp.

The *E. coli* sequence of Ppc has been deposited in the NCBI database as NP 418391. Methods of obtaining a desired gene from bacterial cells are common and well known in the art of molecular biology. For example, if a sequence of a gene is known, suitable genomic libraries may be created and screened. Once a sequence is isolated the DNA may be amplified using standard techniques such as polymerase chain reaction (PCR) (U.S. Pat. No. 4,683,202) to obtain amounts of DNA by restriction. Also reference is made to Sambrook et al., supra. Additionally publicly available computer programs can be used to determine sequences with identity to a Ppc. Preferred programs include the GCG Pileup program, FASTA (Pearson et al. (1988) *Proc. Natl. Acad. Sci. USA* 85:2444-2448) and BLAST (*BLAST Manual*, Altschul et al., Natl. Cent. Biotechnol. Inf., Natl Library Med. (NCBI NLM), NIH, Bethesda Md. and Altschul et al., (1997) *NAR* 25:3389-3402).

Once a DNA integration cassette for ppc overexpression is constructed it may be introduced into a host cell as described above for the DNA mutagenic cassette. The engineered cell preferably expresses ppc at a level higher than the level of ppc expressed in a comparable wild-type cell. This comparison can be made in any number of ways by one of skill in the art and is done under comparable growth conditions. For example, Ppc enzymatic activity can be quantified and compared using various assays known to those skilled in the art. For example, Ppc activity can be quantified using cell free extracts by a coupled assay (Flores and Gancedo 1997). This method involves incubating at room temperature a ultracentifuged (50,000 rpm, 1 h, 4° C.) cell free extract sample in a cuvette that contain 0.22 mM NADH, 1.1 mM phosphoenolpyruvate (PEP), 0.25 mM acetyl-CoA, and 6 U of malate dehydrogenase (MDH) in 0.1 M Tris/HCl, pH 8.5 buffer with 11 mM sodium bicarbonate and 11 mM magnesium sulfate, in a total volume of 1.0 mL. A background rate of the reaction of enzyme and NADH is first determined at 340 nm. The second substrate, PEP, is subsequently added and the absorbance change over time is further monitored. PPC activity is defined by subtracting the background rate from the gross rate.

E. Inactivation of Other Genes

Methods as described above may be used to inactivate other genes, and engineered bacterial strains according to the invention may be further modified to include these inactivated genes.

Inactivation of edd

Catabolism of gluconate via the Entner-Doudoroff pathway is controlled by the GntR regulon. It has been identified as being located at 1931.7 *E. coli*. (Conway, et al. (1991) *J. Bacteriol.*, 173:5247-5248 and Rgan et al. (1992) *J. Bacteriol.* 174:4638-4646). Gluconate is the only carbon source known to require the edd gene product for efficient metabolism. (Sweeney et al., (1996) *Infect. Immun.* 64:3497-3503). The edd gene (NCBI AAC74921) encodes 6-phosphogluconate dehydrase (EC 4.2.1.12) which converts gluconate-6-phosphate into pyruvate and glyceraldehydes-3-phosphate in the catabolism of gluconate. (Peekhaus & Conway, (1998) *J. Bact.*, 180: 3495-3502). It has been observed that the inactivation of edd does not preclude growth on gluconate and that gluconate metabolism will occur through the pentose pathway. The participation of the Entner-Doudoroff pathway in cells growing on glucose as the only carbon source has not been reported. However, considering that under those conditions, the majority of the carbon is assimilated through the glycolytic pathway and only a small percentage of the carbon goes to the pentose pathway, the participation of the Entner-Doudoroff pathway in glucose assimilation (if any), has been perceived to be minimal. Glucose metabolism through the Entner-Doudoroff pathway is less efficient in the production of energy because by forming directly one molecule of pyruvate and one molecule of glyceraldehydes-3-phosphate, skips the formation of other intermediates like Fructose 1,6 biphosphate and Fructose 6-phosphate, forcing the cells to synthesize these intermediates through gluconogenic reactions that are more costly from the energetic point of view. Therefore in one embodiment it could an advantageous to further engineer host cells to have a nonfunctional edd.

The absence of the phosphogluconate dehydratase catalyzed end products would indicate the inactivation of the gene. For example, phosphogluconate dehydratase enzymatic activity can be quantified and compared using various assays known to those skilled in the art. For example, Edd activity can be quantified using HPLC methods (Taha et al., (1994) *Analytical Biochemistry* 219:115-120).

Inactivation of pta and ackA

In many bacteria that are metabolizing glucose at a high rate under aerobic conditions, the carbon flow exceeding the capacity of the TCA cycle is converted to acetic acid for secretion outside of the cells. In *E. coli*, acetate is formed from Acetyl-CoA by the action of 2 enzymes: phosphotransacetylase (E.C. 2.3.1.8) and acetate kinase (E.C. 2.7.2.1), encoded by the pta (NCBI entry AE000319) and ackA (NCBI entry AE000318) genes respectively. It has been reported that the inactivation of the pta and ackA genes does not eliminate the formation of acetate completely. (Ricci et al., (1991) *Biotechnol. Bioeng.* 38: 1318-1324). Furthermore, the inactivation of these genes caused the secretion of other organic acids like lactate and pyruvate, and in general, it had a negative effect on the metabolism of *E. coli* under both aerobic and anaerobic culture conditions (Diaz-Ricci et al., (1991) *Biotechnol. Bioeng.* 39: 1318-1324). However, the elimination of the acetate pathway could have a beneficial impact on a fermentation process.

Phosphotransacetylase enzymatic activity can be quantified and compared using various assays known to those skilled in the art. (De Spiegeleer, Bart, et al, *Anal. Biochem.* (1986), 158(1), 195-200).

Inactivation of mgsA

The widespread occurrence of the methylglyoxal pathways in bacteria suggested that it may function as a bypass of the glycolytic pathway by converting dehydroxyacetone phosphate (an intermediate of the upper part of the glycolytic pathway) into pyruvate. However, in *E. coli*, it has been shown that the methylglyoxal pathway can not replace non-functional glycolytic pathway reaction such as glyceraldehyde-3-phosphate dehydrogenase, triosephosphate isomerase, phosphoglycerate kinase or enolase. (Cooper R. A., (1984) *Ann. Rev. Microbiol.* 38: 49-68). These results seem to indicate that the methylglyoxal pathway is not involved in glucose metabolism for growth. Considering that methylglyoxal is produced in all cells by a variety of mechanisms, and that methylglyoxal is a highly reactive compound with a strong toxic effect, this pathway has been seen as a detoxification mechanism (Ferguson et al., *Arch. Microbiol.* 170: 209-219 (1998) and Ferguson G. P. *Trends Microbiol.* 7: 242-247 (1999)). However, it may be advantageous to inactivate the mgsA gene (NCBI AE000198) which encodes a methylglyoxal synthase enzyme (E.C. 2.1.1.21), that converts dehydroxyacetone phosphate into methylglyoxal, and inactivation of the gene may eliminating unnecessary formation of methylglyoxal by this enzyme. (see FIG. 2)

As described above in this disclosure, homologous genes of edd, ackA, pta and mgsA in other species or strains can be obtained by generating cDNA from RNA from such species using any technique known in the art, such as using Riboclone cDNA Synthesis Systems AMV RT (Promega, Madison, Wis.); hybridization studies, and computer alignment programs.

F. Cell Cultures and Fermentations

Methods suitable for the maintenance and growth of bacterial cells are well known and reference is made to the MANUAL OF METHODS OF GENERAL BACTERIOLOGY, Eds. P. Gerhardt et al., American Society for Microbiology, Washington D.C. (1981) and T. D. Brock in BIOTECHNOLOGY: A TEXTBOOK OF INDUSTRIAL MICROBIOLOGY, 2nd ed. (1989) Sinauer Associates, Sunderland, Mass.

Cell Precultures

Typically cell cultures are grown at 25 to 32° C. and preferably about 28 or 29° C. in appropriate media. While the examples describe growth media used, other exemplary growth media useful in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. Suitable pH ranges preferred for the fermentation are between pH 5 to pH 8 where pH 7 to pH 7.5 for the seed flasks and between pH 5 to pH 6 for the reactor vessel.

It will be appreciated by one of skill in the art of fermentation microbiology that, now that Applicants have demonstrated the feasibility of the process of the present invention a number of factors affecting the fermentation processes may have to be optimized and controlled in order to maximize the ascorbic acid intermediate production. Many of these factors such as pH, carbon source concentration, and dissolved oxygen levels may affect the enzymatic process depending on the cell types used for ascorbic acid intermediate production.

Fermentation Media:

Fermentation media in the present invention must contain suitable carbon substrates which will include but are not limited to monosaccharides such as glucose and fructose, oligosaccharides such as lactose or sucrose, polysaccharides such as starch or cellulose and unpurified mixtures from a renewable feedstocks such as cheese whey permeate, corn-steep liquor, sugar beet molasses, and barley malt. Additionally the carbon substrate may also be one-carbon substrates such as carbon. Although it is contemplated that all of the above mentioned carbon substrates are suitable in the present invention preferred are the carbohydrates glucose, fructose or sucrose. In one embodiment, the concentration of the carbon substrate is from about 55% to about 75% on a weight/weight basis and also from about 60 to about 70% on a weight/weight basis. In addition to an appropriate carbon source, fermentation media must contain suitable minerals, salts, vitamins, cofactors and buffers suitable for the growth or the cultures and promotion of the enzymatic pathway necessary for ascorbic acid intermediate production.

Batch and Continuous Fermentations:

The present process employs a fed-batch method of fermentation for its culture systems. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous Fermentations:

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation.

Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for ascorbic acid intermediate production.

G. Identification and Purification of Desired Products

The presence of desired products and produced end-products can be verified by running a HPLC analysis. Samples can be drawn at predetermined time periods and analyzed for the presence or quantity of a specific product or intermediate. For example, samples can be periodically drawn off the fermentation reactor vessel and loaded onto Dionex (Sunnyvale, Calif., Product No. 043118) Ion Pac AS 10 column (4 mm times 250 mm) connected to a Waters 2690 Separation Module and a Waters 410 Differential Refractometer (Milford, Mass.).

A method of determining the production efficiency of the modified host cell is an analysis of the substrate consumption or of $CO_2$ production. As used herein, "Oxygen Uptake Rate or "OUR" refers to the determination of the specific consumption of oxygen within the reactor vessel. Oxygen consumption can be determined using various on-line measurements. In one example, the OUR (mmol/(liter*hour)) is determined by the following formula: ((Airflow (standing liters per minute)/Fermentation weight (weight of the fermentation broth in kilograms))×supply $O_2$×broth density×(a constant to correct for airflow calibration at 21.1 C instead of standard 20.0 C)) minus ([airflow/fermentation weight]×[offgas $O_2$/offgas $N_2$]×supply $N_2$×broth density×constant).

Carbon evolution rate (CER) refers to the determination of how much $CO_2$ is produced within the reactor vessel during fermentation. Usually, since no $CO_2$ is initially or subsequently provided to the reaction vessel, any $CO_2$ is assumed to be produced by the fermentation process occurring within the reaction vessel. "Off-gas $CO_2$" refers to the amount of $CO_2$ measured within the reactor vessel, usually by mass spectroscopic methods known in the art. As used herein, "yield" refers to the amount of product/the amount of substrate. The yield can be expressed as a weight % (product gm/substrate gm) or as moles of product/moles of substrate. For example, the amount of the substrate, e.g., glucose, can be determined by the feed rate and the concentration of the added glucose. The amount of products present can be determined by various spectrophotometer or analytic methodologies. One such methodology is high performance liquid chromatography (HPLC). An increased yield refers to an increased yield as compared to the yield of a conversion using the wild-type organism, for example an increase of at least 5%, 10%, 20%, 30%, 40%, 50% 75%, 90% over the yield of the wild-type. In addition, those skilled in the art will recognize that assays can be used to determine the amounts and/or presence of glucose and desired products. such as glycerol, 1,3-propanediol.

Methods for the purification of the desired end products or intermediates from fermentation media are known in the art. Desired products include succinate, glycerol, 1,3-propanediol, chorismate, pyruvate, ethanol, acetate and ascorbic acid (ASA) intermediates, such as gluconate, 2-keto-D-gluconic acid (2 KDG), 2, 5DKG and 2-keto-L-gulonic acid (2KLG).

A protein is substantially pure when at least about 60% to 75% of a sample exhibits a single polypeptide sequence. A substantially pure protein typically comprises about 60 to 90% by weight of a protein sample, more usually about 95% and preferably at least 96%, 97%, 98% and 99%.

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

The invention is better understood by reference to the following examples, which merely illustrate but not limit the best mode now known for practicing the invention.

General Methods

Methods used for the construction of chromosomal modifications in *E. coli* strains are described below.

Isolation of *E. coli* chromosomal DNA was as performed using the commercial kit UltraClean (MoBio Lab. Inc. Solana Beach, Calif.). To transform *E. coli* strains with PCR products, cells were grown and made competent by the procedure described by Datsenko & Wanner ((2000) *Proc. Natl. Acad. Sci.* 97: 6640-6645). Transformants carrying the plasmid were grown in 5-ml SOB cultures (Hanahan, D (1983) *J. Mol. Biol.* 166, 557-580) with ampicillin and L-arabinose at 30 C to an OD600 of ≈0.6 and them made electro competent by concentrating 100-fold and washing three times with ice-cold 10% glycerol. Plasmid DNA transformation in *E. coli* strains was done by electroporation of competent cells prepared as described by Sambrook, supra.

Different products of cellular metabolism or media components like glycerol, glucose and 1,3-propanediol (3PG), compounds, were quantified by HPLC as described by Emptage et al., in PCT publication WO 01/12833-A1. The conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 $NH_2SO_4$ as mobile phase at a flow rate of 0.5 mL/min. When quantitative analysis was desired, samples were prepared with a known amount of trimethylacetic acid as an external standard.

Gene Disruptions

To integrate DNA into a specific region of the chromosome, homology of the inserting DNA to the targeted chromosomal site and a selectable marker are required. Preferably the marker will be removed after integration. The loxP/Cre recombinase system from P1phage and the FRT/Flp recombinase system from yeast provide a mechanism to remove the marker. The DNA mutagenic cassettes containing homologous nucleic acid sequences of the regulatory region encoding the expression of the global regulators to be inactivated and a selectable marker flanked by loxP (Palmeros et al. (2000) *Gene* 247:255-264) or FRT (Datsenko and Wanner (2000) *Proc. Natl. Acad. Sci. USA* 97:6640-6645) sites is transformed by electroporation into a target host cell harboring pKD46 (Datsenko and Wanner, supra). Transformants are selected by growth of the cells in the presence of the antibiotic. Subsequently, pKD46 is cured from the cells and recombinase plasmids are introduced into the transformants for removal of the selectable marker. Strain integrated with a loxP cassette are transformed with pJW168 that encodes Cre recombinase (Palmeros et al., supra). Strain containing a FRT cassette are transformed with pCP20 that encodes Flp recombinase (Datsenko and Wanner, supra). After removal of the integrated selectable marker, the recombinase plasmids are cured from the strain.

P1 vir transduction was preformed as described in Miller, J. H. A Short Course in Bacterial Genetics. A Laboratory Manual and Handbook for *Escherichia coli* and related Bacteria (1992) Cold Spring Harbor Laboratory, Cold Spring Harbor, N.Y.

Primers and PCR Verification

Nucleic acid primers based on arcA, edd, ackA, pta, mgsA, pckA and ppc sequences can be prepared by standard techniques. Primers can be used, for example, for amplification of nucleic acid sequences, e.g., by the polymerase chain reaction (PCR). See, e.g., PCR Protocols: A Guide to Methods and Applications, Innis et al., eds., Academic Press: San Diego (1990). The preparation and use of probes and primers is described, e.g., in Sambrook et al. (1989) or Ausubel et al. (1987).

Three PCR reactions were used to confirm that mutants had the correct structure. A freshly isolated colony was suspended in 20 microliters of water with and 5 μl portions were used in separate 20 μl PCR reactions following a 2-minute preincubation, "hot start", at 95° C. Common test primers included those set forth in FIG. 3. A reaction was carried out with flanking locus-specific primers to verify simultaneous loss of the parental (wildtype) fragment and gain of the new specific exogenous fragment. The later was repeated after elimination of the selective marker, the antibiotic resistance gene. Control colonies were always tested side by side.

Construction of the pSYCO Constructs.

The utility of the PTS$^-$/Glu$^+$ strains to convert carbon from glucose to a product was tested by plasmids carrying genes encoding enzymes that carry out conversion of DHAP to 1,3 propanediol. The pSYCO constructs were pSC101 (Stratagene) based plasmids that carry genes for conversion of DHAP (dihydroxyacetone-P) to glycerol (dar1 and gpp2) from *Saccharomyces cerevisiae* (referred to as the glycerol pathway) and subsequently glycerol to 1,3-propanediol (dhaB1-3, dhaX, orfW, X, and Y from *Klebsiella*, (referred to as the 1,3-propanediol pathway). The pSYCO constructs used in the current examples were pSYCO101, 103, 106 and 109 and reference is made to FIGS. 6 and 7 which depict the nucleotide sequence and plasmid map of pSYCO 101, respectively. The pSYCO103 construct is identical to pSYCO101 except the DNA region which includes the glycerol pathway genes and the two EcoR1 sites in the opposite orientation to that of pSYCO101. The pSYCO106 construct is identical to pSYCO103 except for the removal of the 126 bp of non-coding plasmid DNA between the EcoR1 sites and bp 10589-11145. The pSYCO109 construct is identical to pSYCO 106 except that the coding region orfW has been deleted. For the experiments described herein, the plasmids are functionally equivalent.

EXAMPLE 1

A. Deletion of the arcA Gene

The arcA gene was deleted in 2 *E. coli* strains: MG1655 (ATCC 47076) and strain KLNDH which is a derivative of strain KLP23 described by Emptage et al (PCT publication WO 01/12833-A1) where the ndh gene has been inactivated. To inactivate the arcA gene, the procedure described by Datsenko & Wanner was utilized (Datsenko & Wanner (2000) *Proc. Natl. Acad. Sci. USA,* 10: 6640-6645). Briefly, the method uses a plasmid that codes for 3 protein activities that increase the frequency of homologous recombination. These activities allow the use of small regions of homology 36 to 50 nucleotides long, to promote the homologous recombination between the chromosome and a DNA mutagenic cassette. A PCR reaction is used to generate the mutagenic cassette that contains the regions of homology with the chromosome at both ends. In this particular example, the arcA mutagenic cassette was obtained by PCR using plasmid pKD3 (see below) and the primers ArcA1 and ArcA2 (SEQ ID NO. 1 and SEQ ID NO. 2) that contain regions of homology to the arcA gene and to the FRT-cat cassette present in pKD3. This plasmid has been described by Datsenko & Wanner, supra.

The proper integration of the arcA mutagenic cassette was confirmed by sequencing the chromosomal region using primers ArcA3 and ArcA4 (SEQ ID NO. 3 and SEQ ID NO.4).

B. Effect of the arcA Deletion

To evaluate the impact of the deletion of the arcA gene in strain MG1655, the growth of the strain was evaluated in shake flasks. For such a purpose, 250 ml flasks containing 10 ml of minimal media TM2 [TM2 medium (g/L): $K_2HPO_4$ (13.6 g/l), $KH_2PO_4$ (13.6 g/l), $MgSO_4.7H_2O$ (2 g/l), citric acid monohydrate (2 g/l), ferric ammonium citrate (0.3 g/l), $(NH_4)_2SO_4$ (3.2 g/l), yeast extract (5 g/l), solution of trace elements (1 ml), pH adjusted to 6.8. The solution of trace elements contained (g/L): citric acid. $H_2O$ (4.0 g/l), $MnSO_4.H_2O$ (3.0) g/l, NaCl (1.0 g/l), $FeSO_4.7H_2O$ (0.10 g/l), $CoCl_2.6H_2O$ (0.10 g/l), $ZnSO_4.7H_2O$ (0.10 g/l), $CuSO_4.5H_2O$ (0.010 g/l), $H_3BO_3$ (0.010 g/l), and $Na_2MoO_4.2H_2O$ (0.010 g/l)] supplemented with 2% glucose, were inoculated to a 1/200 dilution with an overnight culture of the strain MG1655 (wildtype-wt) and MG1655 ΔarcA grown in LB (5 g/L yeast extract, 10 g/L tryptone, and 10 g/L NaCl). Cultures were incubated at 37° C. in a orbital shaker PsycroTherm (New Brunswick, Edison, N.J. USA) at 275 rpm. Samples were taken at different time intervals and the Optical density (OD) at 600 nm was measured. Cells were removed by centrifugation and the supernatants were utilized to quantify glucose and acetate. Cultures were grown under medium, atmospheric pressure and temperature, such that dissolved oxygen was not limiting. For example at 34° C. and atmospheric pressure of 760 mmHg, in $H_2O$ the dissolved $O_2$ is 7 mg/ml. Conditions in medium will be lower (Vesilind, P. A. (1996) INTRODUCTION TO ENVIRONMENTAL ENGINEERING, PWS Publishing Company Boston, Mass. Table 6.2-6).

As shown in FIGS. 4a and 4b compared to the MG1655 strain, strain MG1655 with the arcA deletion (ΔarcA) grew to a higher cell density ($OD_{600}$ of 35 versus 25) and produced less acetate (approximately 1 g/l compared to 9 g/l). These results indicate that the ΔarcA strain was more efficient in converting media components into biomass, with less acetate as a metabolism by-product.

To evaluate the impact of the arcA deletion (ΔarcA) in the production of a chemical compound, strains KLNDH (FM5 glpK-gldA-ndn) and KLNDH ΔarcA were transformed with plasmid pSYCO101 (FIGS. 6 and 7) which carries the genes to convert dihydroacetone-phosphate into glycerol. Strain FM5 is disclosed in U.S. Pat. No. 5,494,816 and U.S. Pat. No. 6,136,576 and reference is also made to ATCC Accession no. 53911. The resulting strains, KLNDH ΔarcA 101 and KLNDH 101 were evaluated as described above in example 1b, except that the production of glycerol was also measured. As shown in table 1, compared to KLNDH, KLNDH ΔarcA strain produced more glycerol (28.7 compared to 22.5 g/l) and was more efficient for the conversion of glucose into product (Molar yield=moles of product obtained per mole of glucose consumed) than the wildtype strain (1.32 compared to 1.02).

TABLE 1

| STRAIN | Glycerol g/L | Molar Yield |
| --- | --- | --- |
| KLNDN 101 | 22.5 | 1.02 |
| KLNDH ΔarcA 101 | 28.7 | 1.32 |

EXAMPLE 2

A. Inactivation of the rpoS Gene

The rpoS gene was inactivated in strain KLP23 (Empage et al., WO 01/12833) by transduction. A P1-lysate from strain JM101-rpoS::Tn10 was prepared by standard methods. This strain contains the rpoS::Tn10 loci from strain AMS150 described by McCann et al., (1991) *J. Bacteriol.* 173: 4188-4194. The P1-lysate was used to transduce the Tn 10 marker into KLP23. Transductants were selected on Lb plates containing 20 micrograms/ml of Tetracycline. Colonies that appeared after 16-20 hrs. at 37° C. were further purified by streaking them onto fresh Tetracycline plates. Single colonies where checked for a decrease on hydrogen-peroxidase activity using the bubbling test (Chou et al., (1996) *Biotechnol. Bioeng.* 50: 636-642).

B. Effect of the rpoS::TN10 Mutation

To evaluate the effect of rpoS inactivation, a KLP23 rpoS::Tn10 strain was transformed with plasmid pAH48 that codes for 2 yeast genes that convert dehydroxyacetone phosphate into glycerol (Emptage et al PCT publication WO 01/2833-A). The resulting strain KLP23 rpoS/48 was analyzed as described in example 1B. As can be seen on FIG. 5, the inactivation of rpoS had a positive effect on glycerol production by increasing the conversion of glucose into glycerol (yield).

EXAMPLE 3

A. Overexpression of the ppc Gene

To alter the regulation of the ppc gene, its native regulatory region was replaced by a synthetic construction that includes the strong promoter 1.6-GI (SEQ ID NO. 19). The ppc natural promoter was replaced by the short 1.6 GI promoter (SEQ ID NO. 20) in FMP'1.5gapAmgsA (genotype FM5 glpk-gldA-ndh-ptsHIcrr-galPp-trc glkptrc arcA-edd-gapAp-1.5 mgsA-).

Construction of the 1.5gapA in FMP' is as follows: The native gapA promoter was replaced with a synthetic short 1.5 GI promoter (SEQ ID NO. 22) by replacing 225 bp of upstream gapA sequence (see GeneBank Accession No. U00096)) with FRT-CmR-FRT and engineered promoter. The replacement cassette was amplified by PCR with the primer pair SEQ ID NO. 23 and SEQ ID NO. 24 using pKD3 as a template. The primer SEQ ID NO. 23 contains 39 bp of homology to gapA including the ATG start, the short 1.5GI promoter and 20 bp of homology to template pKD3. Primer SEQ ID NO. 24 contains 59 bp of homology to upstream gapA sequence and 21 bp of homology to pKD3. The PCR products were gel-purified and electroporated into MG1655/pKD46 competent cells to give MG1655 1.5gapA::Cm. Recombinant cells were selected on LB plates with 12.5 mg/L chloramphenicol. Successful integration of the cassette replaces the region 34-258 bp upstream of the gapA ATG start codon with a FRT-CmR-FRT-short 1.5 GI promoter cassette. A P1 phage lystae was prepared and used to move to mutation to FMP'::Km. This strain was designated FMP'::Km 1.5gapA::Cm.

The short 1.5 GI gapA promoter in MG1655 1.5 gapA::Cm was replaced with a 1.6 GI promoter (SEQ ID NO. 20). To create the 1.6gapA strain, a replacement cassette was PCR amplified with primer pair SEQ ID NO. 25 and SEQ ID NO. 26 using genomic DNA from MG1655 1.5gapA::Cm as template. The primer SEQ ID NO. 26 contains homology to the gapA upstream region in MG1655 1.5 gapA::Cm and contains the 1.6 GI promoter (SEQ ID NO. 20). The 1.6 GI promoter replacement cassette was used to replace the native gapA promoter of MG1655 as described above to give strain MG1655 1.6gapA::Cm. This strain was then used to replace the natural gapA promoter of FMP'::Km (using P1 transduction) to give strain FMP'::Km 1.6gapA::Cm. Glyceraldehyde-3-phosphate dehydrogenase activity was determined using cell-free extracts prepared from FMP'::Km1.5gapA::Cm, FMP'::Km 1.6gapA::Cm and FMP'::Km as control. The values obtained compared to that of the control. The strain FMP'::Km 1.6gapA::Cm was transformed with the plasmid pSYCO106.

Two sets of primers were used. The ppcR (SEQ ID NO. 17) primer is 100 nucleotides long and includes the entire sequence from the +1 of P1 (natural ppc promoter) and transcription start to 41 bp upstream the ATG of ppc; the 1.6 GI promoter sequence from 4 bp upstream the −35 to 9 bp downstream the −10 and the priming site for pKD3. The ppcF primer (SEQ ID NO. 18) is 80 bp long and contains 59 bp of sequence (1860478 to 1860536) from the intergenic region and the priming site for pKD3.

The PCR primer utilized to amplify the excisable antibiotic marker, carries besides the regions of homology with the chromosome and the antibiotic cassette, the 1.6 GI promoter.

Once the proper genomic modification was corroborated by sequencing, the level of Phosphoenolpyruvate carboxylase (Ppc) enzymatic activity was measured from cell free extracts obtained from the shake flasks described in example 1. Aliquots of cells were harvested in mid-log phase, broken by two passages through a French press cell, centrifuged for 15 min at 14,000 rpm, and ultracentrifuged 1 hr at 50,000 rpm. The supernatant was removed and used as a source of proteins. Specific activities of Ppc are reported in Table 2. The replacement of the natural ppc promoter with the short 1.6 GI promoter (SEQ ID NO. 20) increased the Ppc enzyme activity by three fold.

TABLE 2

| STRAIN | OD | PEP carboxylase specific activity U/mg protein) |
| --- | --- | --- |
| FMP'1.5gap ΔmgsA, pSYCO106 | 11.3 | 0.28 |
| FMP'1.5gap Δmgs 1.6 ppc, pSYCO106 | 9.3 | 0.86 |

B. Effect of Overexpressing the ppc Gene

Shake flask cultures were used to assess the conversion of glucose to 1,3-propanediol in *E. coli* strains FMP'1.5gap Δmgs/pSYCO106 and FMP'1.5gap Δmgs 1.6 ppc/pSYCO106.

The strains, grown in LB medium containing 50 mg/L spectinomycin for 10 hrs, were used to inoculated (200 μl) into 250 ml-baffled Erlenmeyer flasks containing 10 ml TM2 medium, 20 g/L glucose, 50 mg/L spectinomycin, and 2 mg/L vitamin B12.

The flasks were incubated at 300 rpm and 34° C. Representative results are given in Table 3. Both an increase in the molar yield and a decrease of acetate production were observed with the addition of the 1.6 ppc mutation to the parent strain.

TABLE 3

| Strain | OD$_{550}$ | Glucose consumed (g/L) | Glycerol produced (g/L) | 1,3-propanediol produced (g/L) | Acetate produced (g/L) | Molar Yield |
|---|---|---|---|---|---|---|
| FMP'1.5gap ΔmgsA/pSYCO106 | 5.1 | 17.1 | 8.24 | 2.19 | 1.78 | 1.25 |
| FMP'1.5gap ΔmgsA 1.6 ppc/SYCO106 | 12.5 | 17.1 | 7.5 | 3.34 | 0.34 | 1.32 |

EXAMPLE 4

A. Deletion of the edd Gene

The same procedure described for the deletion of arcA was used to inactivate the edd gene, except that the Cat cassette was obtained from plasmid pLoxCat2 described by Palmeros et al., (Palmeros et al. (2000) Gene 247:255-264). The primers edd1 and edd2 (SEQ ID. NO. 5 and SEQ ID NO. 6) utilized to generate the mutagenic cassette which contained 80 bases of homology to the eddgene and 20 bases to pLox-Cat2.

The edd gene was deleted in strain KLGG ΔarcA (FM5 glpK-gldA-ndh-ptsHIcrr-KmR galPp-trc glkp-trc arcA-). Proper integration of the cassette was confirmed by sequencing the chromosomal region using primers edd3 and edd4 SEQ ID NO. 7 and SEQ ID NO. 8.

B. Effect of the Deletion of edd

To evaluate the impact of the edd deletion in the production of a chemical compound, strains KLGG ΔarcA, and KLGG ΔarcA Δedd were transformed with plasmid pSYCO103 that carries the genes to convert dihydroacetone-phosphate into glycerol, and glycerol into 1,3, propanediol in the presence of vitamin B-12. The resulting strains KLGG ΔarcA/103, and KLGG ΔarcA Δedd/101 were evaluated as described in Example 2, except that the production of glycerol and 1,3 propanediol was measured. As shown in table 4, compared with the ΔarcA strain, the Δedd strain produced more glycerol and 1,3 propanediol. Furthermore, it was more efficient for the conversion of glucose into products (Molar yield=moles of product obtained per mole of glucose).

TABLE 4

| Strain | OD$_{550}$ | Glucose consumed | Glycerol (g/L) | 1,3-propanediol (g/L) | Molar yield | Titer Glycerol + 1,3-propanediol |
|---|---|---|---|---|---|---|
| LGGΔarcA/103 | 5.2 | 4.51 | 1.77 | 1.14 | 1.44 | 2.91 |
| KLGGΔarcA/Δedd/103 | 5.9 | 5.82 | 2.36 | 2.14 | 1.7 | 4.5 |

EXAMPLE 5

A. Deletion of the mgsA

Deletion of the mgsA gene was performed as described above for arcA. The primers mgsA-1 (SEQ ID NO. 13) and mgsA-2 (SEQ ID NO. 14) were utilized to generate the mutagenic DNA cassette, which contained 36 bases of homology to the mgsA gene, and 20 bases of homology to pKD4. Plasmid pKD4 has been described by Datsenko & Wanner, supra. The mgsA gene was deleted in strain FMP'1.5gapA (FM5 glpk-gldA-ndh-ptsHIcrr-galPp-trc glkp-trc arcA-edd-gapAp-1.5). Proper integration of the DNA cassette was confirmed by sequencing the chromosomal region using primers mgsA-3 (SEQ ID NO. 15) and mgsA-4 (SEQ ID NO. 16).

B. Effect of the mgsA Deletion

To evaluate the impact of the mgsA deletion in the production of a chemical compound, strains FMP'1.5gap and FMP'1.5gap ΔmgsA were transformed with plasmid pSYCO106 that carries the genes to convert dihydroacetone-phosphate into glycerol, and glycerol into 1,3, propanediol in the presence of vitamin B-12. The resulting strains were evaluated as described in example 1B, except that the production of glycerol and 1,3 propanediol was measured. As shown in table 5, compared with the parent strain the ΔmgsA strain produced more glycerol and 1,3 propanediol. The cell efficiency improvement due to the mgsA mutation was more visible at the Molar yield obtained (see Table 5).

TABLE 5

| Strain | glycerol + 1,3 propanediol (g/L) | glucose consumed (g/L) | Molar Yield (mol/mol) |
|---|---|---|---|
| FMP'1.5gapA/pSYCO106 | 10.2 | 17.6 | 1.21 |
| FMP'1.5gapΔmgsA/pSYCO106 | 10.7 | 17.1 | 1.26 |

Molar Yield = moles of product formed per moles substrate used.

EXAMPLE 6

A. Deletion of the ackA-pta Genes

The ackA and pta genes are contiguous in the E. coli chromosome and deletion of these genes was performed as described above for arcA. The primers DacA-F (SEQ ID NO. 9) and Dpta-R (SEQ ID NO. 10) were utilized to generate a mutagenic DNA cassette which contained 80 bases of homology to the ackA or pta genes respectively, and 20 bases of homology to pKD3.

The ackA and pta genes were deleted in strain Triple1.6 btuR1.6yqhD (FM5 glpk-gldA-ndh-ptsHIcrr-galPp-trc glkp-trc arcA-edd-gapAp-1.5 mgsA-ppcp-1.6 yciK-btu Rp-1.6 yqhC-yqhDp-1.6).

The proper integration of the cassette was confirmed by sequencing the chromosomal region using primers ackU (SEQ ID NO. 11) and ackD (SEQ ID NO. 12). The resulting strain Triple1.6 btuR1.6yqhDackA-pta and the parent were transformed with pSYCO109.

The strains were grown as described above except that the stability of the plasmid was examined by growing the strains in the presence or absence of spectinomycin (concentration of 100 micrograms/ml) and passing the culture every 24 hours by adding 16 microliters of the previous days culture to a fresh batch of medium and allowing the strain to grow. This sequential dilution of the culture was repeated every day for 5 days and samples were taken on a daily basis to assess the production of glycerol and 1,3-propanediol. Typically in the absence of spectinomycin in the culture, the pSYCO 109 plasmid would be quickly lost upon passage of the culture.

B. Effect of the ack-pta Deletion

TABLE 6

| Strain | Spect | MY-D1 | MY-D2 | MY-D3 | MY-D4 | MY-D5 |
|---|---|---|---|---|---|---|
| TriplebtuR 1.6yqhD, pSYCO109 | + | 1.24 | 1.28 | 1.06 | 0.84 | 0.79 |
| TriplebtuR 1.6yqhD, Δack-pta, pSYCO109 | + | 1.15 | 1.22 | 1.24 | 1.24 | 1.07 |
| TriplebtuR 1.6yqhD, pSYCO109 | − | 1.23 | 1.04 | 0.95 | 0.61 | 0.25 |
| TriplebtuR 1.6yqhD, Δack-pta, pSYCO109 | − | 1.23 | 1.22 | 1.23 | 1.13 | 1.11 |

MY = Molar Yield (moles of product formed per moles substrate used); DX = Day 1, 2, 3, 4 or 5 and Spec (+/−) means with or with spectinomycin.

In the presence of spectinomycin, the parent strain exhibits a 15% decline in molar yield by day 3 and a 38% decline by day 5 indicating that even in the presence of antibiotic, the production of glycerol and 1,3-propanediol is negatively affected by continuous passage of the culture. With the deletion of ack-pta, the molar yield declines by only 0.07% after 5 days, indicating a significant increase in stability of production. This effect is even more pronounced in the absence of antibiotic. By day 5, the parent strain showed a 80% decrease in molar yield while the strain with the deletion of ack-pta showed only a 0.1% decrease in molar yield. Thus the deletion of these two genes significantly increased the stability of the plasmid and production of glycerol and 1,3-propanediol.

SEQUENCE LISTING

```
<160> NUMBER OF SEQ ID NOS: 26

<210> SEQ ID NO 1
<211> LENGTH: 61
<212> TYPE: DNA
<213> ORGANISM: Artificial Sequence
<220> FEATURE:
<223> OTHER INFORMATION: synthetic primer

<400> SEQUENCE: 1
cacattctta tcgttgaaga cgagttggta acacgcaaca cgtgtaggct ggagctgctt     60
c                                                                    61

<210> SEQ ID NO 2
<211> LENGTH: 62
<212> TYPE: DNA
<213> ORGANISM: Artificial Sequence
<220> FEATURE:
<223> OTHER INFORMATION: synthetic primer

<400> SEQUENCE: 2
ttccagatca ccgcagaagc gataaccttc accgtgaatg gtcatatgaa tatcctcctt     60
ag                                                                   62

<210> SEQ ID NO 3
<211> LENGTH: 24
<212> TYPE: DNA
<213> ORGANISM: Artificial Sequence
```

```
<220> FEATURE:
<223> OTHER INFORMATION: synthetic primer

<400> SEQUENCE: 3
agttggtaac acgcaacacg caac                                          24

<210> SEQ ID NO 4
<211> LENGTH: 23
<212> TYPE: DNA
<213> ORGANISM: Artificial Sequence
<220> FEATURE:
<223> OTHER INFORMATION: synthetic primer

<400> SEQUENCE: 4
cgcagaagcg ataaccttca ccg                                           23

<210> SEQ ID NO 5
<211> LENGTH: 99
<212> TYPE: DNA
<213> ORGANISM: Artificial Sequence
<220> FEATURE:
<223> OTHER INFORMATION: synthetic primer

<400> SEQUENCE: 5
atgaatccac aattgttacg cgtaacaaat cgaatcattg aacgttcgcg cgagactcgc   60
tctgcttatc tcgcccggat ttatcgataa gctggatcc                          99

<210> SEQ ID NO 6
<211> LENGTH: 98
<212> TYPE: DNA
<213> ORGANISM: Artificial Sequence
<220> FEATURE:
<223> OTHER INFORMATION: synthetic primer

<400> SEQUENCE: 6
ttaaaaagtg atacaggttg cgccctgttc ggcaccggac agttttttcac gcaaggcgct  60 gaataattca cgtcctgtcg gatgcatatg gcggccgc                           98

<210> SEQ ID NO 7
<211> LENGTH: 22
<212> TYPE: DNA
<213> ORGANISM: Artificial Sequence
<220> FEATURE:
<223> OTHER INFORMATION: synthetic primer

<400> SEQUENCE: 7
taacatgatc ttgcgcagat tg                                            22

<210> SEQ ID NO 8
<211> LENGTH: 21
<212> TYPE: DNA
<213> ORGANISM: Artificial Sequence
<220> FEATURE:
<223> OTHER INFORMATION: synthetic primer

<400> SEQUENCE: 8
actgcacact cggtacgcag a                                             21

<210> SEQ ID NO 9
<211> LENGTH: 100
<212> TYPE: DNA
<213> ORGANISM: Artificial Sequence
<220> FEATURE:
<223> OTHER INFORMATION: synthetic primer
```

<400> SEQUENCE: 9
atgtcgagta agttagtact ggttctgaac tgcggtagtt cttcactgaa atttgccatc    60
atcgatgcag taaatggtga tgtgtaggct ggagctgctt                          100

<210> SEQ ID NO 10
<211> LENGTH: 100
<212> TYPE: DNA
<213> ORGANISM: Artificial Sequence
<220> FEATURE:
<223> OTHER INFORMATION: synthetic primer

<400> SEQUENCE: 10
ttactgctgc tgtgcagact gaatcgcagt cagcgcgatg gtgtagacga tatcgtcaac    60
cagtgcgcca cgggacaggt catatgaata tcctccttag                          100

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
attcattgag tcgtcaaatt                                                20

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
attgcggaca tagcgcaaat                                                20

<210> SEQ ID NO 13
<211> LENGTH: 60
<212> TYPE: DNA
<213> ORGANISM: Artificial Sequence
<220> FEATURE:
<223> OTHER INFORMATION: synthetic primer

<400> SEQUENCE: 13
gtacattatg gaactgacga ctcgcacttt acctgcgcgg tgtaggctgg agctgcttcg    60

<210> SEQ ID NO 14
<211> LENGTH: 60
<212> TYPE: DNA
<213> ORGANISM: Artificial Sequence
<220> FEATURE:
<223> OTHER INFORMATION: synthetic primer

<400> SEQUENCE: 14
cttcagacgg tccgcgagat aacgctgata atcggggatc catatgaata tcctccttag    60

<210> SEQ ID NO 15
<211> LENGTH: 22
<212> TYPE: DNA
<213> ORGANISM: Artificial Sequence
<220> FEATURE:
<223> OTHER INFORMATION: synthetic primer

<400> SEQUENCE: 15
cttgaattgt tggatggcga tg                                             22

```
<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
cgtcacgtta ttggatgaga g                                              21

<210> SEQ ID NO 17
<211> LENGTH: 100
<212> TYPE: DNA
<213> ORGANISM: Artificial Sequence
<220> FEATURE:
<223> OTHER INFORMATION: synthetic primer

<400> SEQUENCE: 17
tcgcattggc gcgaatatgc tcgggctttg cttttcgtca gtggttgaat tatttgctca    60
ggatgtggca ttgtcaaggg catatgaata tcctccttag                         100

<210> SEQ ID NO 18
<211> LENGTH: 100
<212> TYPE: DNA
<213> ORGANISM: Artificial Sequence
<220> FEATURE:
<223> OTHER INFORMATION: synthetic primer

<400> SEQUENCE: 18
cgatttttta acatttccat aagttacgct tatttaaagc gtcgtgaatt taatgacgta    60
aattcctgct atttattcgt gtgtaggctg gagctgcttc                         100

<210> SEQ ID NO 19
<211> LENGTH: 44
<212> TYPE: DNA
<213> ORGANISM: Artificial Sequence
<220> FEATURE:
<223> OTHER INFORMATION: synthetic promoter

<400> SEQUENCE: 19
cgagccgtca cgcccttgac aatgccacat cctgagcaaa taat                     44

<210> SEQ ID NO 20
<211> LENGTH: 42
<212> TYPE: DNA
<213> ORGANISM: Artificial Sequence
<220> FEATURE:
<223> OTHER INFORMATION: synthetic promoter

<400> SEQUENCE: 20
gcccttgaca atgccacatc ctgagcaaat aattcaacca ct                       42

<210> SEQ ID NO 21
<211> LENGTH: 13669
<212> TYPE: DNA
<213> ORGANISM: Artificial Sequence
<220> FEATURE:
<223> OTHER INFORMATION: synthetic plasmid pSYCO101

<400> SEQUENCE: 21
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
```

```
ttagtgcatc taacgcttga gttaagccgc gccgcgaagc ggcgtcggct tgaacgaatt      240
gttagacatt atttgccgac taccttggtg atctcgcctt tcacgtagtg gacaaattct      300
tccaactgat ctgcgcgcga ggccaagcga tcttcttctt gtccaagata agcctgtcta      360
gcttcaagta tgacgggctg atactgggcc ggcaggcgct ccattgccca gtcggcagcg      420
acatccttcg gcgcgatttt gccggttact gcgctgtacc aaatgcggga caacgtaagc      480
actacatttc gctcatcgcc agcccagtcg ggcggcgagt tccatagcgt taaggtttca      540
tttagcgcct caaatagatc ctgttcagga accggatcaa agagttcctc cgccgctgga      600
cctaccaagg caacgctatg ttctcttgct tttgtcagca agatagccag atcaatgtcg      660
atcgtggctg gctcgaagat acctgcaaga atgtcattgc gctgccattc tccaaattgc      720
agttcgcgct tagctggata cgccacggaa tgatgtcgt cgtgcacaac aatggtgact      780
tctacagcgc ggagaatctc gctctctcca ggggaagccg aagtttccaa aaggtcgttg      840
atcaaagctc gccgcgttgt ttcatcaagc cttacggtca ccgtaaccag caaatcaata      900
tcactgtgtg gcttcaggcc gccatccact gcggagccgt acaaatgtac ggccagcaac      960
gtcggttcga gatggcgctc gatgacgcca actacctctg atagttgagt cgatacttcg     1020
gcgatcaccg cttccctcat gatgtttaac tttgttttag ggcgactgcc ctgctgcgta     1080
acatcgttgc tgctccataa catcaaacat cgacccacgg cgtaacgcgc ttgctgcttg     1140
gatgcccgag gcatagactg taccccaaaa aaacagtcat aacaagccat gaaaaccgcc     1200
actgcgccgt taccaccgct gcgttcggtc aaggttctgg accagttgcg tgagcgcata     1260
cgctacttgc attacagctt acgaaccgaa caggcttatg tccactgggt tcgtgccttc     1320 atccgttttcc acggtgtgcg tcacccggca accttgggca gcagcgaagt cgaggcattt     1380
ctgtcctggc tggcgaacga gcgcaaggtt tcggtctcca cgcatcgtca ggcattggcg     1440
gccttgctgt tcttctacgg caaggtgctg tgcacggatc tgccctggct tcaggagatc     1500
ggaagacctc ggccgtcgcg gcgcttgccg gtggtgctga ccccggatga agtggttcgc     1560
atcctcggtt ttctggaagg cgagcatcgt ttgttcgccc agcttctgta tggaacgggc     1620
atgcggatca gtgagggttt gcaactgcgg gtcaaggatc tggatttcga tcacggcacg     1680
atcatcgtgc gggagggcaa gggctccaag gatcgggcct tgatgttacc cgagagcttg     1740
gcacccagcc tgcgcagca ggggaattaa ttcccacggg ttttgctgcc cgcaaacggg     1800
ctgttctggt gttgctagtt tgttatcaga atcgcagatc cggcttcagc cggtttgccg     1860
gctgaaagcg ctatttcttc cagaattgcc atgattttttt ccccacggga ggcgtcactg     1920
gctcccgtgt tgtcggcagc tttgattcga taagcagcat cgcctgtttc aggctgtcta     1980
tgtgtgactg ttgagctgta acaagttgtc tcaggtgttc aatttcatgt tctagttgct     2040 ttgtttttact ggtttcacct gttctattag gtgttacatg ctgttcatct gttacattgt     2100
cgatctgttc atggtgaaca gctttgaatg caccaaaaac tcgtaaaagc tctgatgtat     2160
ctatcttttt tacaccgttt tcatctgtgc atatggacag ttttcccttt gatatgtaac     2220
ggtgaacagt tgttctactt ttgtttgtta gtcttgatgc ttcactgata gatacaagag     2280
ccataagaac ctcagatcct tccgtattta gccagtatgt tctctagtgt ggttcgttgt     2340
ttttgcgtga gccatgagaa cgaaccattg agatcatact tactttgcat gtcactcaaa     2400
aattttgcct caaaactggt gagctgaatt tttgcagtta aagcatcgtg tagtgttttt     2460
cttagtccgt tatgtaggta ggaatctgat gtaatggttg ttggtatttt gtcaccattc     2520 attttttatct ggttgttctc aagttcggtt acgagatcca tttgtctatc tagttcaact     2580
```

```
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttttcgct tgagaacttg    2940 gcatagtttg tccactggaa aatctcaaag cctttaacca aaggattcct gatttccaca    3000
gttctcgtca tcagctctct ggttgcttta gctaatacac cataagcatt tccctactg     3060 atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg gctagtcaa     3300 tgataattac tagtcctttt cctttgagtt gtgggtatct gtaaattctg ctagacccttt   3360 gctggaaaac ttgtaaattc tgctagaccc tctgtaaatt ccgctagacc tttgtgtgtt    3420 tttttgttt atattcaagt ggttataatt tatagaataa agaaagaata aaaaagata      3480 aaagaatag atcccagccc tgtgtataac tcactacttt agtcagttcc gcagtattac     3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc tttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttgg ctgttcagca gttcctgccc tctgatttc cagtctgacc     3900 acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttccggag gtaaccaagc ttgcgggaga gaatgatgaa caagagccaa     4260
caagttcaga caatcaccct ggccgccgcc agcaaatgg cggcggcggt ggaaaaaaaa     4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg cgttagcgg cggtacggtc     4620 gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacgaggc ggtgacgccg ctgcgctggg cgcccggcg gccagaagct     4920 cgcccctgcg ggtgggtatc gggctcagcg cgtccggcga gatagccctc actcatgccc    4980
```

```
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880 ttcaccttt gagccgatga acaatgaaaa gatcaaaacg atttgcagta ctggcccagc    5940
gccccgtcaa tcaggacggg ctgattggcg agtggcctga agaggggctg atcgccatgg   6000
acagccccct tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
tgcgtgcccg ccgaccccc tccaaccagt gccacgtcac caatctcaaa gataatccgg    6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg gctattcgg    6720 agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc acctgatgc    6960 agatgctgcc gggcaccgac tttatttct ccggctacag cgcggtgccg aactacgaca    7020
acatgttcgc cggctcgaac ttcgatgcgg aagattttga tgattacaac atcctgcagc   7080
gtgacctgat ggttgacggc ggcctgcgtc cggtgaccga gcggaaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
```

```
tgctgcgcca gcgggtcacc ggcgattacc tgcagacctc ggccattctc gatcggcagt      7440
tcgaggtggt gagtgcggtc aacgacatca atgactatca ggggccgggc accggctatc      7500
gcatctctgc cgaacgctgg gcggagatca aaatattcc gggcgtggtt cagcccgaca       7560
ccattgaata aggcggtatt cctgtgcaac agacaaccca aattcagccc tcttttaccc      7620 tgaaacccg cgagggcggg gtagcttctg ccgatgaacg cgccgatgaa gtggtgatcg       7680
gcgtcggccc tgccttcgat aaacaccagc atcacactct gatcgatatg ccccatggcg      7740
cgatcctcaa agagctgatt gccggggtgg aagaagaggg gcttcacgcc cgggtggtgc      7800
gcattctgcg cacgtccgac gtctccttta tggcctggga tgcggccaac ctgagcggct      7860
cggggatcgg catcggtatc cagtcgaagg ggaccacggt catccatcag cgcgatctgc      7920
tgccgctcag caacctggag ctgttctccc aggcgccgct gctgacgctg agacctacc       7980 ggcagattgg caaaaacgct gcgcgctatg cgcgcaaaga gtcaccttcg ccggtgccgg      8040
tggtgaacga tcagatggtg cggccgaaat ttatggccaa agccgcgcta tttcatatca      8100
aagagaccaa acatgtggtg caggacgccg agcccgtcac cctgcacatc gacttagtaa      8160
gggagtgacc atgagcgaga aaaccatgcg cgtgcaggat tatccgttag ccacccgctg      8220 cccgagcat atcctgacgc ctaccggcaa accattgacc gatattaccc tcgagaaggt       8280
gctctctggc gaggtgggcc cgcaggatgt gcggatctcc cgccagaccc ttgagtacca      8340
ggcgcagatt gccgagcaga tgcagcgcca tgcggtggcg cgcaatttcc gccgcgcggc      8400
ggagcttatc gccattcctg acgagcgcat tctggctatc tataacgcgc tgcgcccgtt      8460
ccgctcctcg caggcggagc tgctggcgat cgccgacgag ctggagcaca cctggcatgc      8520
gacagtgaat gccgccttg tccgggagtc ggcggaagtg tatcagcagc ggcataagct       8580
gcgtaaagga agctaagcgg aggtcagcat gccgttaata gccgggattg atatcggcaa      8640
cgccaccacc gaggtggcgc tggcgtccga ctacccgcag gcgagggcgt tgttgccag       8700 cgggatcgtc gcgacgacgg gcatgaaagg gacgcgggac aatatcgccg ggaccctcgc      8760
cgcgctggag caggccctgg cgaaaacacc gtggtcgatg agcgatgtct ctcgcatcta      8820
tcttaacgaa gccgcgccgg tgattggcga tgtggcgatg gagaccatca ccgagaccat      8880
tatcaccgaa tcgaccatga tcggtcataa cccgcagacg ccgggcgggg tgggcgttgg      8940
cgtggggacg actatcgccc tcgggcggct ggcgacgctg ccggcggcgc agtatgccga      9000
ggggtggatc gtactgattg acgacgccgt cgatttcctt gacgccgtgt ggtggctcaa      9060
tgaggcgctc gaccgggga tcaacgtggt ggcggcgatc ctcaaaaagg acgacggcgt       9120
gctggtgaac aaccgcctgc gtaaaaccct gccggtggtg gatgaagtga cgctgctgga      9180
gcaggtcccc gagggggtaa tggcggcggt ggaagtggcc gcgccgggcc aggtggtgcg      9240
gatcctgtcg aatccctacg ggatcgccac cttcttcggg ctaagcccgg aagagaccca      9300
ggccatcgtc cccatcgccc gcgccctgat tggcaaccgt tccgcggtgg tgctcaagac      9360
cccgcagggg gatgtgcagt cgcgggtgat cccggcgggc aacctctaca ttagcggcga      9420
aaagcgccgc ggagaggccg atgtcgccga gggcgcggaa gccatcatgc aggcgatgag      9480
cgcctgcgct ccggtacgcg acatccgcgg cgaaccgggc acccacgccg gcggcatgct      9540
tgagcgggtg cgcaaggtaa tggcgtccct gaccggccat gagatgagcg cgatatacat      9600
ccaggatctg ctggcggtgg atacgtttat tccgcgcaag gtgcagggcg ggatggccgg      9660
cgagtgcgcc atggagaatg ccgtcgggat ggcggcgatg gtgaaagcgg atcgtctgca      9720
aatgcaggtt atcgcccgcg aactgagcgc ccgactgcag accgaggtgg tggtgggcgg      9780
```

```
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380 gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagagtac tggcgaaagg gggatgtgct gcaaggcgat taagttgggt aacgccaggg   10560
ttttcccagt cacgacgttg taaaacgacg gccagtgaat tcgagctcgg tacccggggc   10620
ggccgcgcta gcgcccgatc cagctggagt ttgtagaaac gcaaaaaggc catccgtcag   10680
gatggccttc tgcttaattt gatgcctggc agtttatggc gggcgtcctg cccgccaccc   10740
tccgggccgt tgcttcgcaa cgttcaaatc cgctcccggc ggatttgtcc tactcaggag   10800
agcgttcacc gacaaacaac agataaaacg aaaggcccag tctttcgact gagcctttcg   10860 tttatttga tgcctggcag ttccctactc tcgcatgggg agaccccaca ctaccatcgg   10920
cgctacggcg tttcacttct gagttcggca tggggtcagg tgggaccacc gcgctactgc   10980
cgccaggcaa attctgtttt atcagaccgc ttctgcgttc tgatttaatc tgtatcaggc   11040
tgaaaatctt ctctcatccg ccaaaacagc caagcttgca tgcctgcagc ccgggttacc   11100
atttcaacag atcgtcctta gcatataagt agtcgtcaaa aatgaattca acttcgtctg   11160
tttcggcatt gtagccgcca actctgatgg attcgtggtt tttgacaatg atgtcacagc   11220 cttttttcctt taggaagtcc aagtcgaaag tagtggcaat accaatgatc ttacaaccgg   11280
cggcttttcc ggcggcaata cctgctggag cgtcttcaaa tactactacc ttagatttgg   11340
aagggtcttg ctcattgatc ggatatccta agccattcct gccctttcaga tatggttctg   11400 gatgaggctt accctgtttg acatcattag cggtaatgaa gtactttggt ctcctgattc   11460
ccagatgctc gaaccatttt tgtgccatat cacgggtacc ggaagttgcc acagcccatt   11520 tctctttttgg tagagcgttc aaagcgttgc acagcttaac tgcacctggg acttcaatgg   11580
atttttcacc gtacttgacc ggaatttcag cttctaattt gttaacatac tcttcattgg   11640
caaagtctgg agcgaactta gcaatggcat caaacgttct ccaaccatgc gagacttgga   11700
taacgtgttc agcatcgaaa taaggtttgt ccttaccgaa atccctccag aatgcagcaa   11760
tggctggttg agagatgata atggtaccgt cgacgtcgaa caaagcggcg ttaactttca   11820
aagatagagg tttagtagtc aatcccataa ttcagtctg tttcctggat ccaataaatc   11880
taatcttcat gtagatctaa ttcttcaatc atgtccggca ggttcttcat tgggtagttg   11940
ttgtaaacga tttggtatac ggcttcaaat aatgggaagt cttcgacaga gccacatgtt   12000
tccaaccatt cgtgaacttc tttgcaggta attaaacctt gagcggattg gccattcaac   12060
aactcctttt cacattccca ggcgtcctta ccagaagtag ccattagcct agcaaccttg   12120
```

```
acgtttctac caccagcgca ggtggtgatc aaatcagcaa caccagcaga ctcttggtag    12180
tatgtttctt ctctagattc tgggaaaaac atttgaccga atctgatgat ctcacccaaa    12240
ccgactcttt ggatggcagc agaagcgttg ttaccccagc ctagaccttc gacgaaacca    12300
caacctaagg caacaacgtt cttcaaagca ccacagatgg agataccagc aacatcttcg    12360
atgacactaa cgtggaagta aggtctgtgg aacaaggcct ttagaacctt atggtcgacg    12420
tccttgccct cgcctctgaa atcctttgga atgtggtaag caactgttgt ttcagaccag    12480
tgttcttgag cgacttcggt ggcaatgtta gcaccagata gagcaccaca ttgaatacct    12540
agttcctcag tgatgtaaga ggatagcaat tggacacctt tagcaccaac ttcaaaaccc    12600
tttagacagg agatagctct gacgtgtgaa tcaacatgac ctttcaattg gctacagata    12660
cggggcaaaa attgatgtgg aatgttgaaa acgatgatgt cgacatcctt gactgaatca    12720
atcaagtctg gattagcaac caaattgtcg ggtagagtga tgccaggcaa gtatttcacg    12780
ttttgatgtc tagtatttat gatttcagtc aattttttcac cattgatctc ttcttcgaac    12840
acccacattt gtactattgg agcgaaaact tctgggtatc ccttacaatt ttcggcaacc    12900
accttggcaa tagtagtacc ccagttacca gatccaatca cagtaacctt gaaaggcttt    12960
tcggcagcct tcaaagaaac agaagaggaa cttctcttct taccagcatt caagtggccg    13020
gaagttaagt ttaatctatc agcagcagca gccatggaat tgtcctcctt actagtcatg    13080
gtctgtttcc tgtgtgaaat tgttatccgc tcacaattcc acacattata cgagccggat    13140
gattaattgt caacagctca tttcagaata tttgccagaa ccgttatgat gtcggcgcaa    13200
aaaacattat ccagaacggg agtgcgcctt gagcgacacg aattatgcag tgatttacga    13260
cctgcacagc cataccacag cttccgatgg ctgcctgacg ccagaagcat tggtgcacgc    13320
tagccagtac atttaaatgg taccctctag tcaaggcctt aagtgagtcg tattacggac    13380
tggccgtcgt tttacaacgt cgtgactggg aaaaccctgg cgttacccaa cttaatcgcc    13440
ttgcagcaca tccccctttc gccagctggc gtaatagcga agaggcccgc accgatcgcc    13500
cttcccaaca gttgcgcagc ctgaatggcg aatggcgcct gatgcggtat tttctcctta    13560
cgcatctgtg cggtatttca caccgcatat ggtgcactct cagtacaatc tgctctgatg    13620
ccgcatagtt aagccagccc cgacacccgc caacacccgc tgacgagct                13669
```

<210> SEQ ID NO 22
<211> LENGTH: 42
<212> TYPE: DNA
<213> ORGANISM: Artificial Sequence
<220> FEATURE:
<223> OTHER INFORMATION: synthetic promoter

<400> SEQUENCE: 22

```
gcccttgact atgccacatc ctgagcaaat aattcaacca ct                          42
```

<210> SEQ ID NO 23
<211> LENGTH: 98
<212> TYPE: DNA
<213> ORGANISM: Artificial Sequence
<220> FEATURE:
<223> OTHER INFORMATION: synthetic primer

<400> SEQUENCE: 23

```
agtcatatat tccaccagct atttgttagt gaataaaagt ggttgaatta tttgctcagg       60
atgtggcata gtcaagggca tatgaatatc ctccttag                               98
```

```
<210> SEQ ID NO 24
<211> LENGTH: 80
<212> TYPE: DNA
<213> ORGANISM: Artificial Sequence
<220> FEATURE:
<223> OTHER INFORMATION: synthetic primer

<400> SEQUENCE: 24
gctcacatta cgtgactgat tctaacaaaa cattaacacc aactggcaaa attttgtccg      60
tgtaggctgg agctgcttcg                                                 80

<210> SEQ ID NO 25
<211> LENGTH: 24
<212> TYPE: DNA
<213> ORGANISM: Artificial Sequence
<220> FEATURE:
<223> OTHER INFORMATION: synthetic primer

<400> SEQUENCE: 25
gtcgacaaac gctggtatac ctca                                            24

<210> SEQ ID NO 26
<211> LENGTH: 98
<212> TYPE: DNA
<213> ORGANISM: Artificial Sequence
<220> FEATURE:
<223> OTHER INFORMATION: synthetic primer

<400> SEQUENCE: 26
agtcatatat tccaccagct atttgttagt gaataaaagt ggttgaatta tttgctcagg     60
atgtggcatt gtcaagggca tatgaatatc ctccttag                             98
```

The invention claimed is:

1. A method of enhancing the production of glycerol in a bacterial host cell comprising, a) modifying a bacterial host cell by inactivating an endogenous arcA gene, b) transforming the host cell with one or more exogenous genes for conversion of dihydroxyacetone-P to glycerol, and c) culturing the modified bacterial host cell in suitable culture media comprising glucose under aerobic conditions to allow enhanced production of glycerol and wherein the bacterial host cell is from a strain of the Enterobacteriaceae family.

2. The method according to claim 1, wherein the bacterial host cell is an *E. coli* or *Pantoea* cell.

3. The method according to claim 1, wherein the bacterial host cell is a PTS$^-$/Glu$^+$ cell.

4. The method according to claim 1 further comprising inactivating the expression of an endogenous gene encoding a polypeptide having RpoS activity, Edd activity, Pta activity, AckA activity or MgsA activity.

5. The method according to claim 1 further comprising transforming the bacterial host cell with a DNA fragment comprising an exogenous promoter, wherein the DNA fragment including the exogenous promoter is integrated into the host cell chromosome and replaces the endogenous promoter which is operably linked to a PEP carboxylase coding sequence wherein PEP carboxylase is overexpressed.

6. The method according to claim 1 further comprising isolating the desired product from the culture media.

7. The modified bacterial host cell obtained according to the method of claim 1.

8. The method of claim 1, wherein the exogenous genes for conversion of dihydroxyacetone-P to glycerol are darl and gpp2 from *Saccharomyces cerevisiae*.

* * * * *